US011730532B2

(12) United States Patent
Krastins et al.

(10) Patent No.: US 11,730,532 B2
(45) Date of Patent: *Aug. 22, 2023

(54) SURGICAL INSTRUMENTS AND METHODS FOR PERFORMING TONSILLECTOMY, ADENOIDECTOMY, AND OTHER SURGICAL PROCEDURES

(71) Applicant: Covidien LP, Mansfield, MA (US)

(72) Inventors: Craig V. Krastins, Arvada, CO (US); James D. Allen, IV, Broomfield, CO (US); Jessica E. C. Olson, Frederick, CO (US); Jason G. Weihe, Longmont, CO (US); Purvish Soni, Longmont, CO (US)

(73) Assignee: Covidien LP, Mansfield, MA (US)

( * ) Notice: Subject to any disclaimer, the term of this patent is extended or adjusted under 35 U.S.C. 154(b) by 297 days.

This patent is subject to a terminal disclaimer.

(21) Appl. No.: 17/065,033

(22) Filed: Oct. 7, 2020

(65) Prior Publication Data
US 2021/0022791 A1    Jan. 28, 2021

Related U.S. Application Data

(63) Continuation of application No. 15/806,679, filed on Nov. 8, 2017, now Pat. No. 10,828,084, which is a
(Continued)

(51) Int. Cl.
*A61B 18/12* (2006.01)
*A61B 17/26* (2006.01)
(Continued)

(52) U.S. Cl.
CPC .............. *A61B 18/12* (2013.01); *A61B 17/26* (2013.01); *A61B 17/29* (2013.01);
(Continued)

(58) Field of Classification Search
CPC ..... A61B 17/0218; A61B 17/26; A61B 17/29; A61B 17/295; A61B 18/12;
(Continued)

(56) References Cited

U.S. PATENT DOCUMENTS 5,445,638 A    8/1995  Rydell et al.
5,458,598 A    10/1995 Feinberg et al.
(Continued)

FOREIGN PATENT DOCUMENTS

AU    2004216575 A1    4/2005
CA       2844067 A1    9/2014
(Continued)

OTHER PUBLICATIONS

Partial European Search Report issued in corresponding European application No. 16170578.5 dated Sep. 1, 2016.
(Continued)

*Primary Examiner* — Michael F Peffley
(74) *Attorney, Agent, or Firm* — Carter, DeLuca & Farrell LLP

(57) ABSTRACT

A surgical instrument includes a housing, a shaft extending therefrom, an end effector assembly supported by the shaft, a movable handle, and a drive assembly. The drive assembly includes a translatable drive member for actuating the end effector assembly, and a torsion spring including first and second legs. The first leg is configured to translate through the housing in response to movement of the movable handle relative to the housing. The second leg is configured to translate through the housing in cooperation with the first leg to move the drive member longitudinally when a force acting on the drive member is less than a threshold force, and to remain in fixed position, thereby tensioning the torsion
(Continued)

spring and retaining the drive member in fixed position when the force acting on the drive member is equal to or exceeds the threshold force.

20 Claims, 29 Drawing Sheets

Related U.S. Application Data continuation of application No. 14/719,422, filed on May 22, 2015, now Pat. No. 9,918,779.

(51) Int. Cl.

| | |
|---|---|
| *A61B 17/29* | (2006.01) |
| *A61B 18/14* | (2006.01) |
| *A61B 90/00* | (2016.01) |
| A61B 18/00 | (2006.01) |
| A61B 17/00 | (2006.01) |
| A61B 17/02 | (2006.01) |
| A61B 17/295 | (2006.01) |
| A61B 17/32 | (2006.01) |

(52) U.S. Cl.
CPC ...... *A61B 18/1445* (2013.01); *A61B 18/1485* (2013.01); *A61B 90/03* (2016.02); *A61B 17/0218* (2013.01); *A61B 17/295* (2013.01); *A61B 18/1447* (2013.01); *A61B 2017/00353* (2013.01); *A61B 2017/00424* (2013.01); *A61B 2017/00526* (2013.01); *A61B 2017/292* (2013.01); *A61B 2017/2912* (2013.01); *A61B 2017/2919* (2013.01); *A61B 2017/2925* (2013.01); *A61B 2017/2926* (2013.01); *A61B 2017/2936* (2013.01); *A61B 2017/320044* (2013.01); *A61B 2018/0091* (2013.01); *A61B 2018/00184* (2013.01); *A61B 2018/00327* (2013.01); *A61B 2018/00607* (2013.01); *A61B 2018/00928* (2013.01); *A61B 2018/1455* (2013.01)

(58) Field of Classification Search
CPC ............ A61B 18/1206; A61B 18/1445; A61B 18/1447; A61B 18/1485; A61B 2017/00353; A61B 2017/00424; A61B 2017/00526; A61B 2017/2845; A61B 2017/2912; A61B 2017/2919; A61B 2017/292; A61B 2017/2925; A61B 2017/2926; A61B 2017/2936; A61B 2017/2945; A61B 2017/320044; A61B 2018/00184; A61B 2018/00327; A61B 2018/00589; A61B 2018/00595; A61B 2018/00607; A61B 2018/0063; A61B 2018/0091; A61B 2018/00928; A61B 2018/1455

See application file for complete search history.

(56) References Cited

U.S. PATENT DOCUMENTS

| | | | |
|---|---|---|---|
| 5,605,272 A | 2/1997 | Witt et al. | |
| 5,683,412 A | 11/1997 | Scarfone | |
| 5,735,849 A * | 4/1998 | Baden ................ | A61B 18/1442 606/205 |
| 5,891,142 A | 4/1999 | Eggers et al. | |
| 5,919,206 A | 7/1999 | Gengler et al. | |
| 5,935,126 A | 8/1999 | Riza | |
| 6,077,287 A | 6/2000 | Taylor et al. | |
| 6,129,740 A | 10/2000 | Michelson | |
| 6,322,579 B1 | 11/2001 | Muller | |
| 6,334,860 B1 | 1/2002 | Dorn | |
| 6,443,968 B1 | 9/2002 | Holthaus et al. | |
| 6,506,208 B2 | 1/2003 | Hunt et al. | |
| 6,706,056 B2 | 3/2004 | Bacher | |
| 6,770,072 B1 | 8/2004 | Truckai et al. | |
| 6,790,217 B2 | 9/2004 | Schulze et al. | |
| 6,887,240 B1 | 5/2005 | Lands et al. | |
| 7,052,496 B2 | 5/2006 | Yamauchi | |
| 7,083,618 B2 * | 8/2006 | Couture ............ | A61B 18/1445 606/49 |
| 7,118,587 B2 * | 10/2006 | Dycus ................ | A61B 18/1445 606/205 |
| 7,147,638 B2 | 12/2006 | Chapman et al. | |
| 7,150,097 B2 | 12/2006 | Sremcich et al. | |
| 7,255,697 B2 | 8/2007 | Dycus et al. | |
| 7,384,420 B2 | 6/2008 | Dycus et al. | |
| 7,491,202 B2 * | 2/2009 | Odom ................ | A61B 18/1445 606/51 |
| 7,494,501 B2 | 2/2009 | Ahlberg et al. | |
| 7,549,988 B2 | 6/2009 | Eberl et al. | |
| 7,559,940 B2 | 7/2009 | McGuire et al. | |
| 7,628,791 B2 | 12/2009 | Garrison et al. | |
| 7,753,909 B2 | 7/2010 | Chapman et al. | |
| 7,758,608 B2 | 7/2010 | DiCesare et al. | |
| 7,766,910 B2 | 8/2010 | Hixson et al. | |
| 7,877,853 B2 | 2/2011 | Unger et al. | |
| 7,922,953 B2 | 4/2011 | Guerra | |
| 8,241,320 B2 | 8/2012 | Lyons et al. | |
| 8,252,021 B2 | 8/2012 | Boulnois et al. | |
| 8,256,080 B2 | 9/2012 | Cunningham et al. | |
| 8,266,783 B2 | 9/2012 | Brandt et al. | |
| 8,388,646 B2 | 3/2013 | Chojin | |
| 8,394,094 B2 | 3/2013 | Edwards et al. | |
| 8,409,244 B2 | 4/2013 | Hinman et al. | |
| 8,545,534 B2 | 10/2013 | Ahlberg et al. | |
| 8,551,090 B2 | 10/2013 | Sutter et al. | |
| 8,728,118 B2 | 5/2014 | Hinman et al. | |
| 8,734,443 B2 | 5/2014 | Hixson et al. | |
| 8,740,933 B2 | 6/2014 | Anderson | |
| 8,789,741 B2 * | 7/2014 | Baxter, III ....... | A61B 17/07207 227/176.1 |
| 8,814,856 B2 | 8/2014 | Elmouelhi et al. | |
| 8,858,553 B2 | 10/2014 | Chojin | |
| 10,828,084 B2 | 11/2020 | Krastins et al. | |
| 11,007,003 B2 * | 5/2021 | Allen, IV ............... | A61B 34/35 |
| 11,026,710 B2 * | 6/2021 | Stamm ................ | A61B 17/295 |
| 2005/0090837 A1 * | 4/2005 | Sixto .................. | A61B 17/1285 606/139 |
| 2007/0074807 A1 | 4/2007 | Guerra | |
| 2010/0063525 A1 | 3/2010 | Beaupre et al. | |
| 2011/0270251 A1 | 11/2011 | Horner et al. | |
| 2012/0215215 A1 | 8/2012 | Reschke | |
| 2012/0215220 A1 | 8/2012 | Manzo et al. | |
| 2013/0296848 A1 * | 11/2013 | Allen, IV ........... | A61B 18/1445 606/41 |
| 2013/0296922 A1 | 11/2013 | Allen, IV et al. | |
| 2014/0025073 A1 | 1/2014 | Twomey et al. | |
| 2014/0257285 A1 * | 9/2014 | Moua .................. | A61B 17/282 606/52 |
| 2014/0316408 A1 | 10/2014 | Davison et al. | |
| 2014/0336628 A1 * | 11/2014 | McFarland ......... | A61B 18/1445 606/206 |
| 2015/0201953 A1 * | 7/2015 | Strobl ................. | A61B 18/1445 606/206 |

FOREIGN PATENT DOCUMENTS

| | | |
|---|---|---|
| EP | 2319447 A1 | 5/2011 |
| EP | 2777586 A1 | 9/2014 |

OTHER PUBLICATIONS

Extended European search report issued in corresponding application No. 16170578.5 dated Dec. 5, 2016.
Examination report issued in corresponding Australian application No. 2016203259 dated Jun. 2, 2017.

(56) References Cited

OTHER PUBLICATIONS

Canadian Office Action issued in corresponding CA application No. 2930309 dated Dec. 7, 2017.
European Search Report dated Jun. 27, 2018, corresponding to European Application No. 18167604.0; 7 pages.
Australian Examination Report dated Aug. 24, 2018, corresponding to counterpart Australian Application No. 2018201955; 2 pages.
Australian Examination Report dated May 16, 2019, corresponding to counterpart Australian Application No. 2019200661; 3 pages.
European Examination Report dated May 4, 2020, correspnding to counterpart European Application No. 18167804.0; 5 pages.
Canadian Office Action issued in corresponding Canadian Application No. 3,029,355 dated Apr. 11, 2023, 3 pages.

* cited by examiner

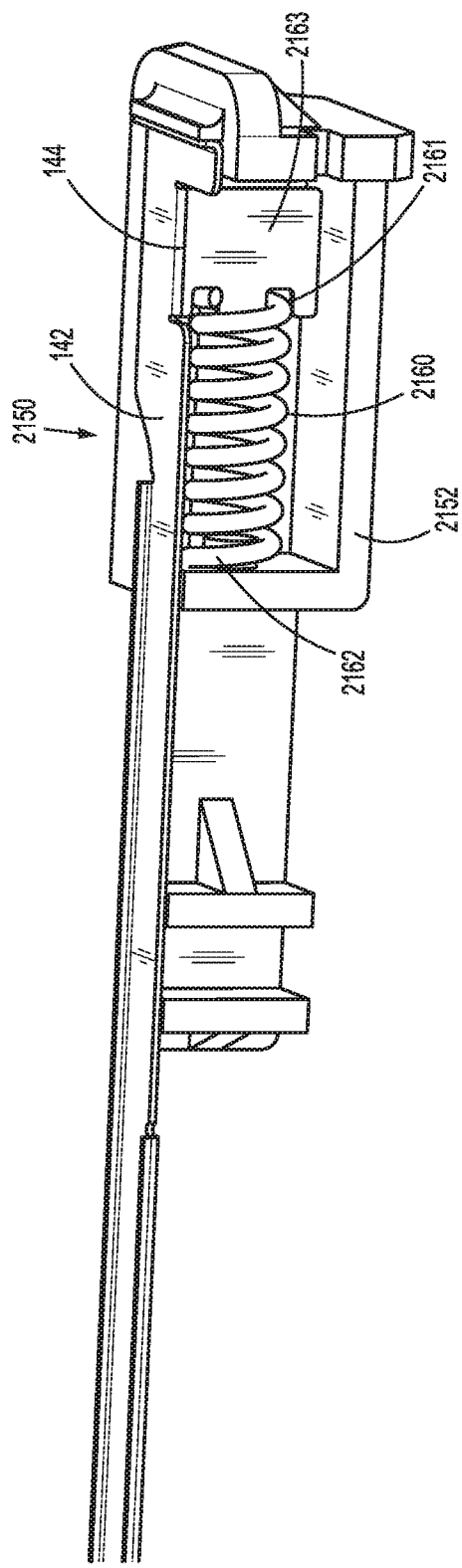

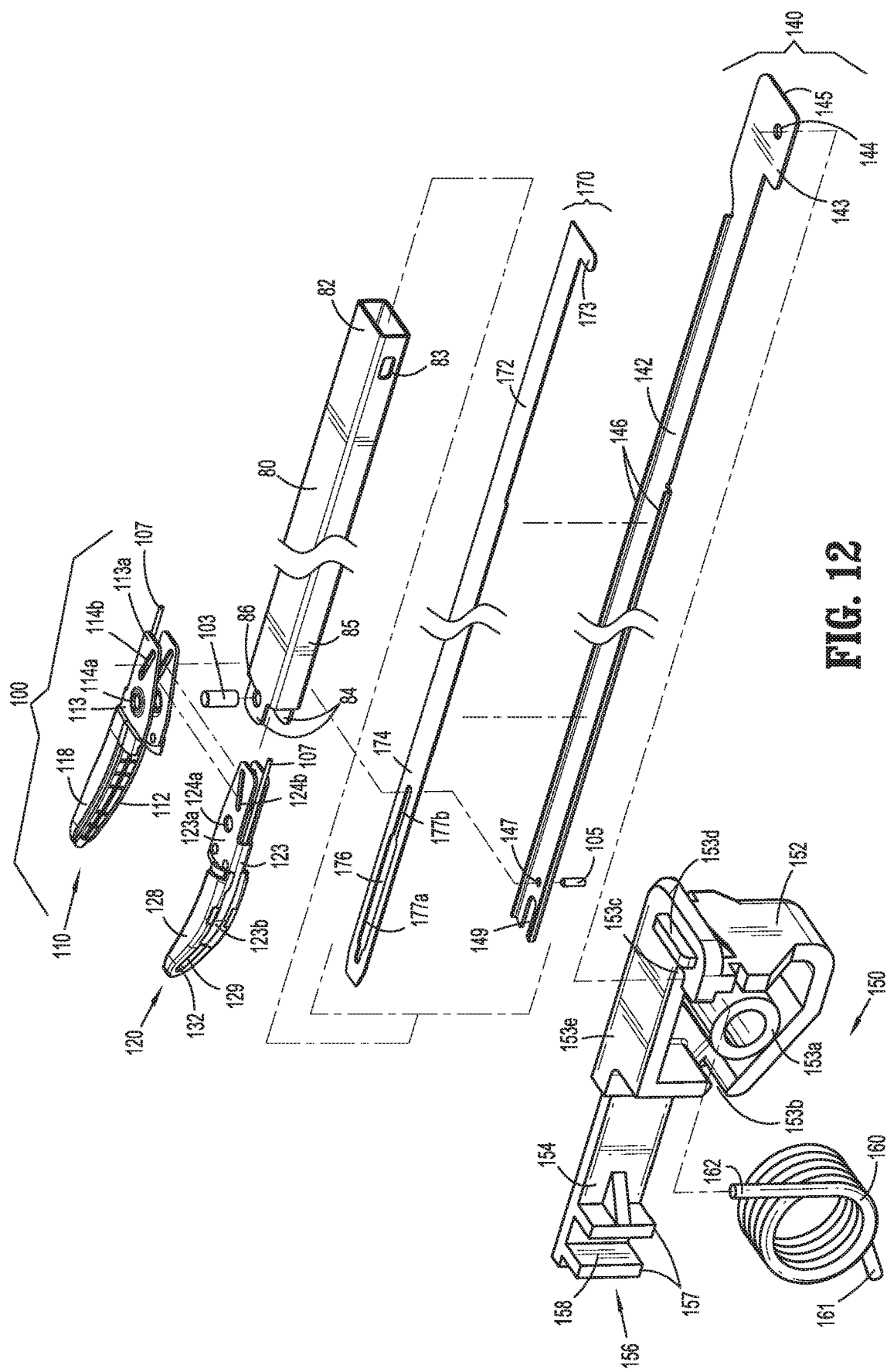

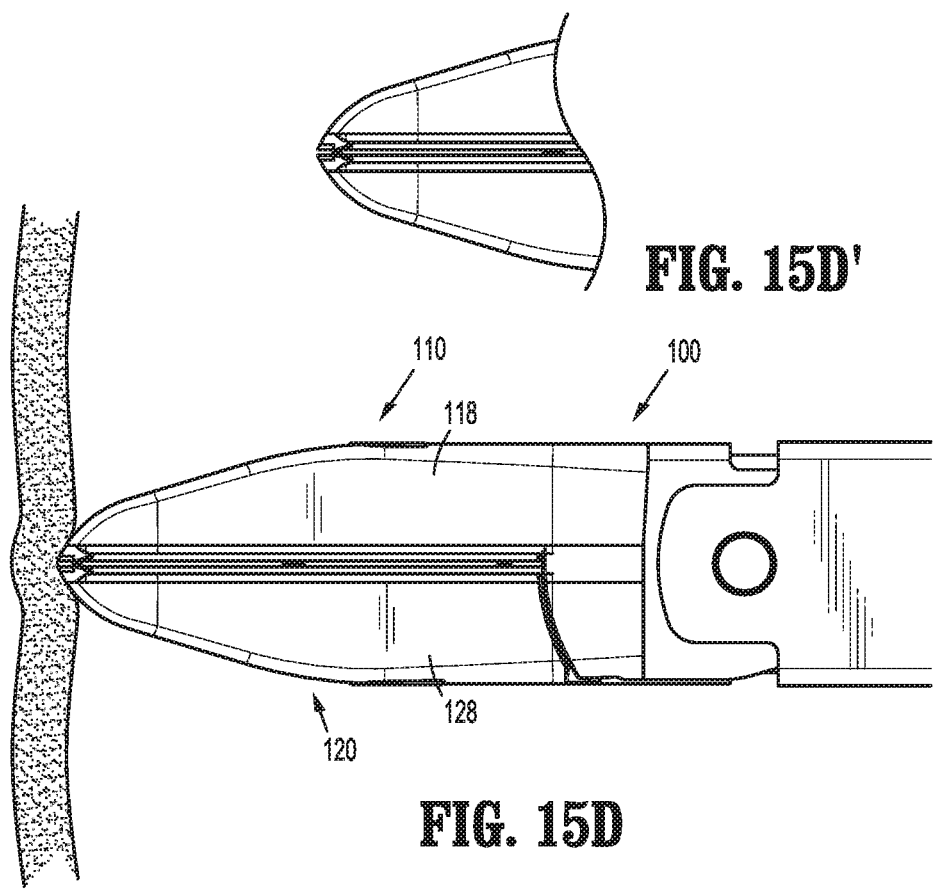
FIG. 15D'
FIG. 15D
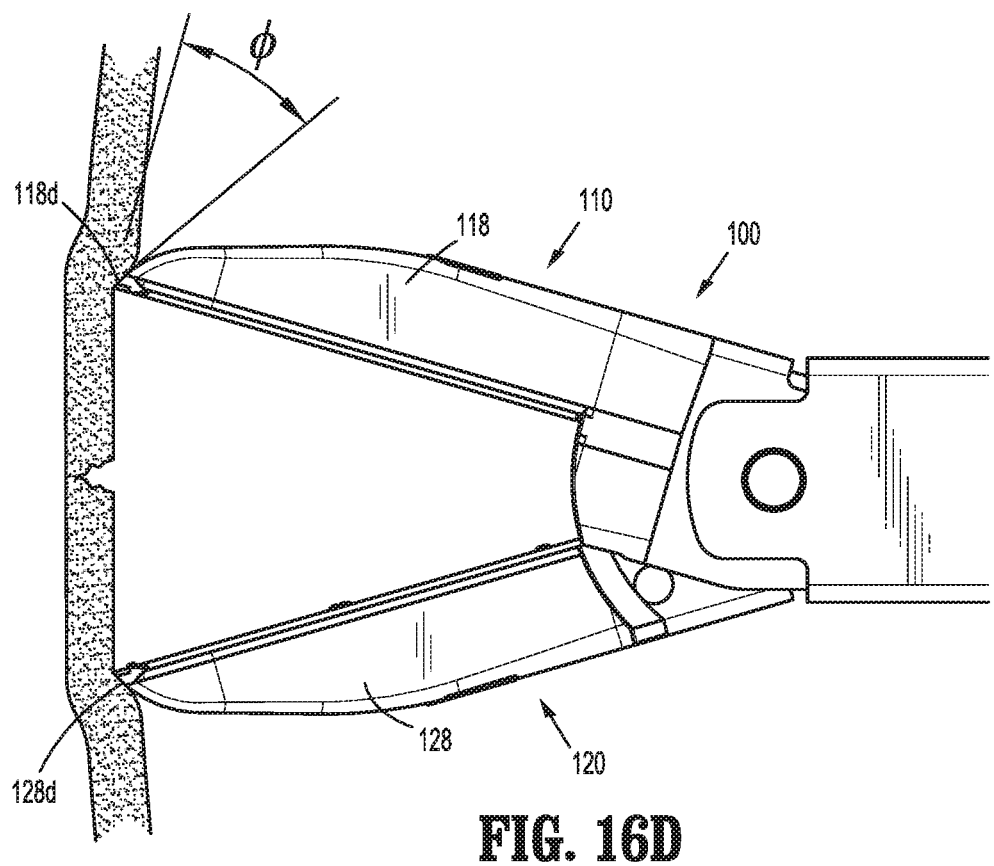
FIG. 16D

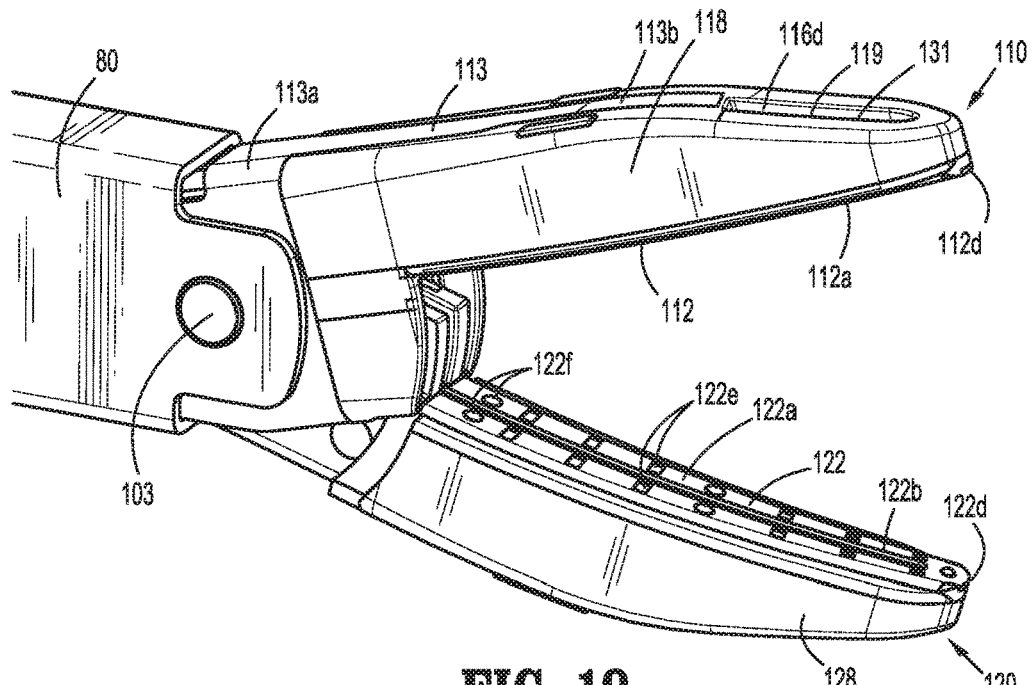
FIG. 19
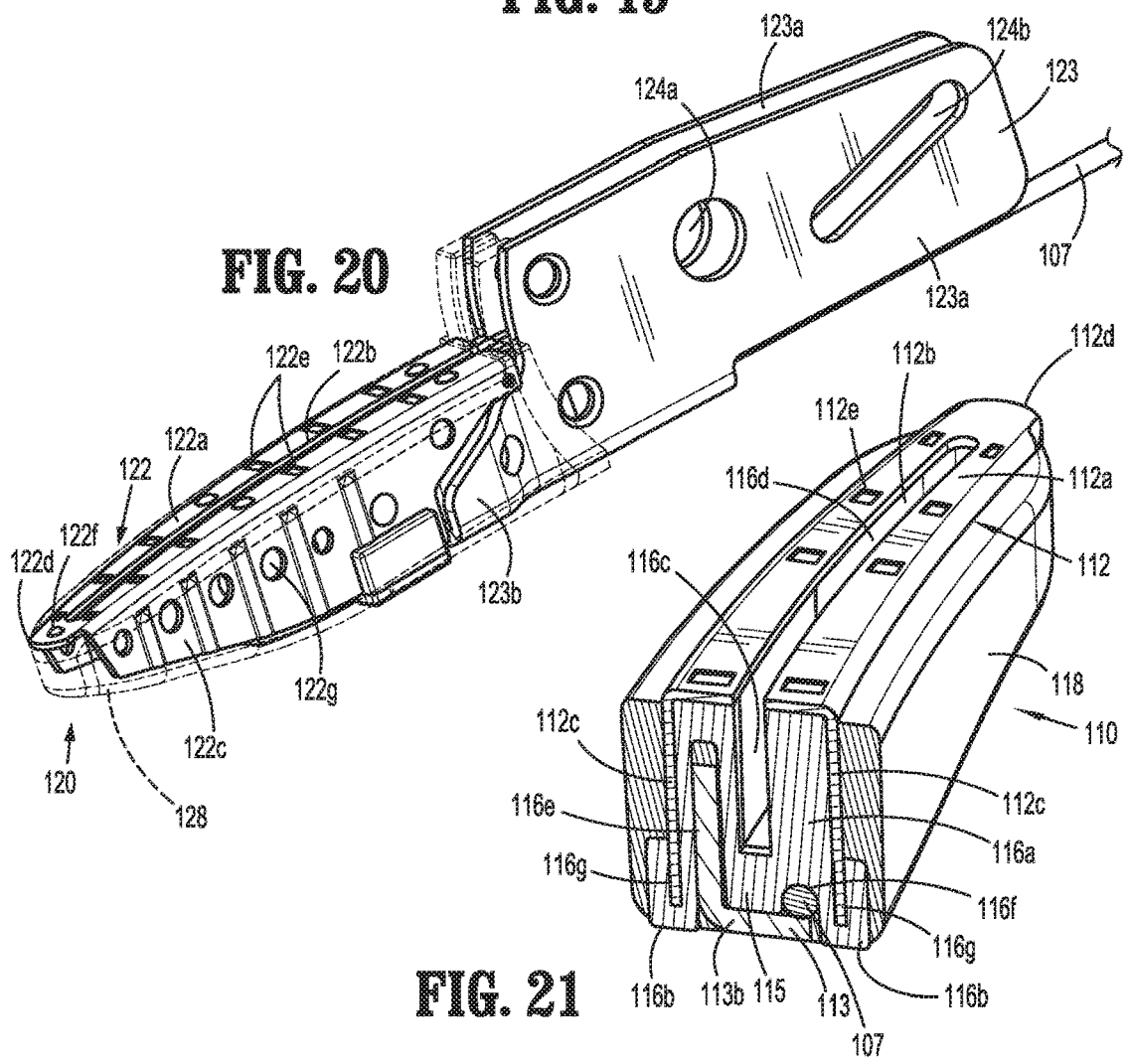
FIG. 20
FIG. 21

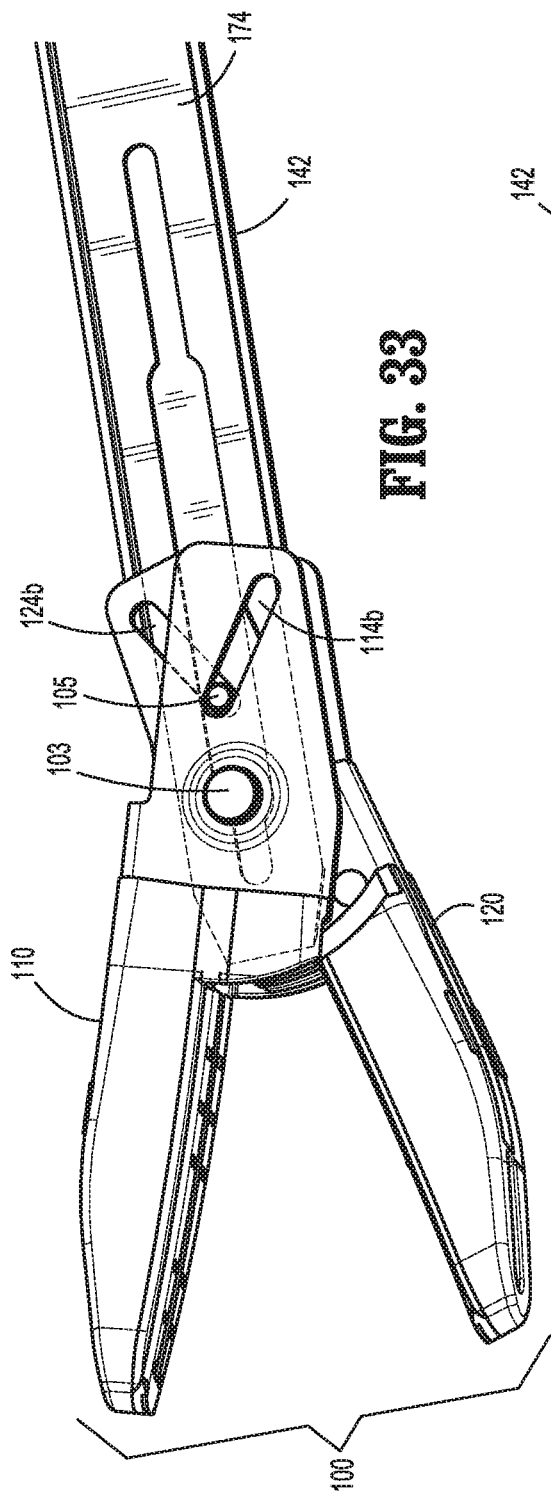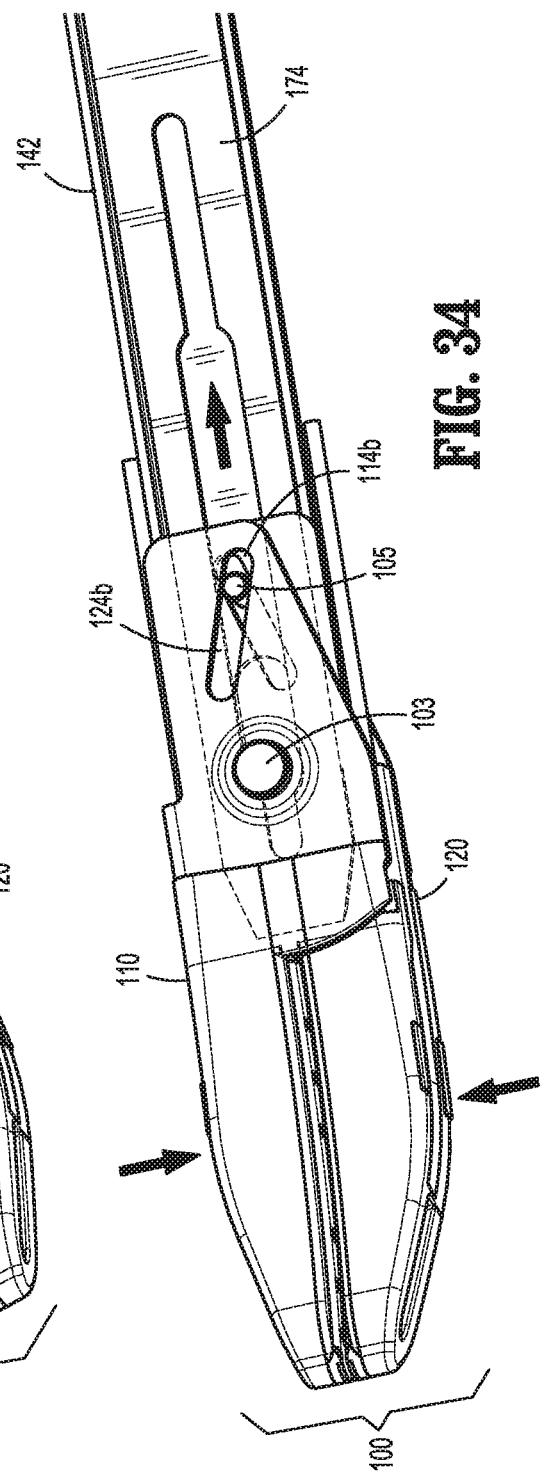

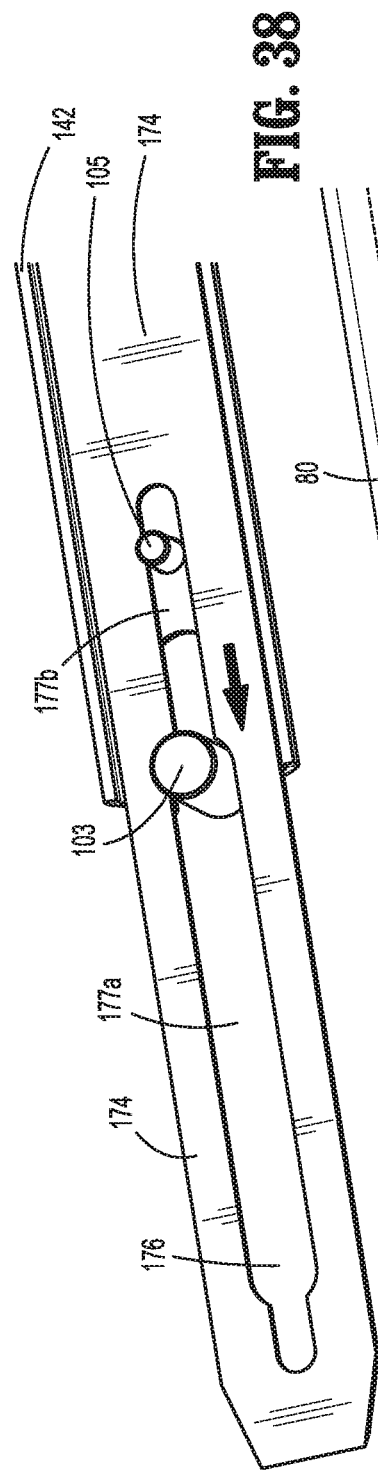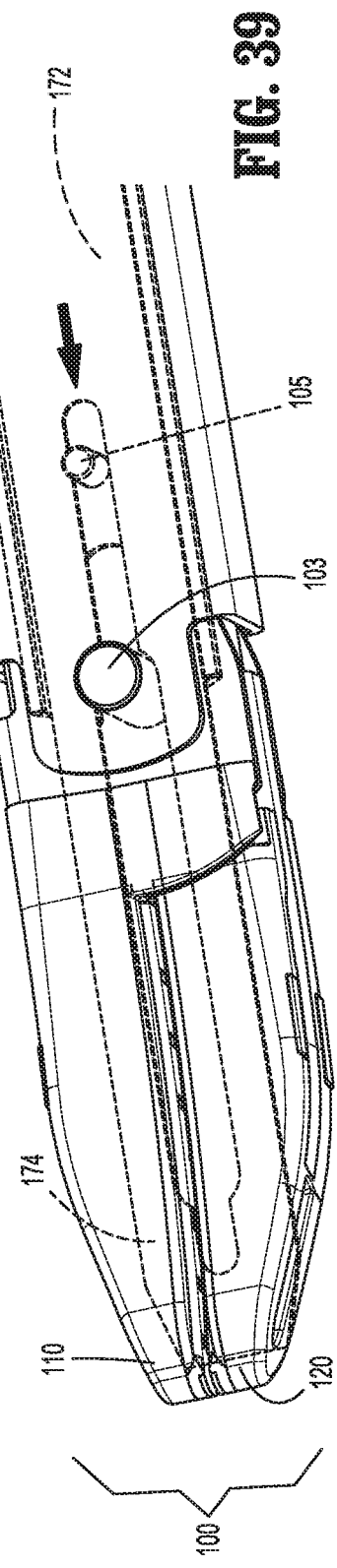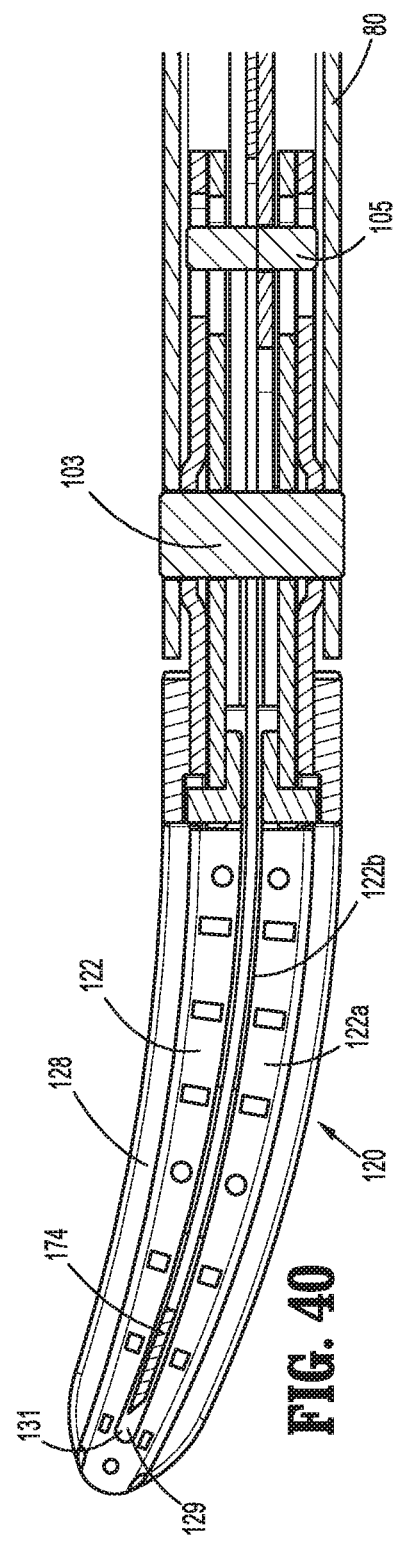

SURGICAL INSTRUMENTS AND METHODS FOR PERFORMING TONSILLECTOMY, ADENOIDECTOMY, AND OTHER SURGICAL PROCEDURES

CROSS-REFERENCE TO RELATED APPLICATIONS

This application is a continuation application of U.S. patent application No. 15/806,679, filed on Nov. 8, 2017, now U.S. Pat. No. 10,828,084, which is a continuation application of U.S. patent application No. 14/719,422, filed on May 22, 2015, now U.S. Pat. No. 9,918,779, the entire contents of each of which are hereby incorporated by reference herein.

BACKGROUND

Technical Field

The present disclosure relates to surgical instruments and methods and, more particularly, to surgical instrument and methods for performing tonsillectomy, adenoidectomy, and other surgical procedures.

Background of Related Art

The tonsils and adenoids are part of the lymphatic system and are generally located in the back of the throat. These parts of the lymphatic system are generally used for sampling bacteria and viruses entering the body and activating the immune system when warranted to produce antibodies to fight oncoming infections. More particularly, the tonsils and adenoids break down the bacteria or virus and send pieces of the bacteria or virus to the immune system to produce antibodies for fighting off infections.

Inflammation of the tonsils and adenoids (e.g., tonsillitis) impedes the ability of the tonsils and adenoids to destroy the bacteria resulting in a bacterial infection. In many instances, the bacteria remain even after treatment and serve as a reservoir for repeated infections (e.g., tonsillitis or ear infections).

A tonsillectomy and/or adenoidectomy may be performed when infections persist and antibiotic treatments fail. Persistent infection typically leads to enlarged tonsil tissue which may need to be removed since in many cases the enlarged tissue causes airway obstruction leading to various sleep disorders such as snoring or, in some cases, sleep apnea. Some individuals are also born with larger tonsils that are more prone to cause obstruction. An adenoidectomy may also be required to remove adenoid tissue when ear pain persists, or when nose breathing or function of the Eustachian tube is impaired. Often times, tonsillectomy and adenoidectomy procedures are performed at the same time.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A surgical instrument provided in accordance with the present disclosure includes a housing, a shaft extending distally from the housing, an end effector assembly coupled at a distal end of the shaft, a movable handle coupled to the housing, and a drive assembly operably coupling the movable handle and the end effector assembly. The drive assembly includes a drive member and a torsion spring. The drive member is configured to translate through the shaft and relative to the end effector assembly to actuate the end effector assembly. The torsion spring includes a first leg and a second leg. The first leg is operably coupled to the movable handle and configured to translate longitudinally through the housing in response to movement of the movable handle relative to the housing. The second leg is operably coupled to the drive member and configured to translate longitudinally through the housing in cooperation with the first leg to thereby transfer longitudinal movement thereof into longitudinal movement of the drive member when a force acting on the drive member is less than a threshold force. The second leg is configured to remain in fixed position, thereby tensioning the torsion spring and retaining the drive member in fixed position, in response to longitudinal movement of the first leg when the force acting on the drive member is equal to or exceeds the threshold force.

In an aspect of the present disclosure, the drive assembly further includes a slider including a housing portion operably retaining the torsion spring therein and a mandrel portion operably coupled to the movable handle. The slider is configured to translate longitudinally through the housing in response to movement of the movable handle relative to the housing.

In another aspect of the present disclosure, the first leg of the torsion spring is engaged with the housing portion of the slider and the second leg of the torsion spring is movable relative to the housing portion of the slider. In such aspects, a body portion of the torsion spring may be rotatably supported on a post disposed within the housing portion of the slider. The post is configured to enable tensioning of the torsion spring in response to movement of the first leg relative to the second leg.

In another aspect of the present disclosure, the first leg of the torsion spring is operably positioned relative to a block disposed within the housing to bias the drive member relative to the housing.

In yet another aspect of the present disclosure, the movable handle is movable relative to the housing between an initial position, a compressed position, and an activated position. The second leg is configured to translate in cooperation with the first leg in response to movement of the movable handle between the initial and compressed positions. The second leg is configured to remain in fixed position in response to movement of the movable handle between the compressed and activated positions.

In still another aspect of the present disclosure, the end effector assembly includes first and second jaw members, at least one of which is movable relative to the other between a spaced-apart position and an approximated position for grasping tissue therebetween. In such aspects, the drive member may be configured to translate through the shaft and relative to the end effector assembly to move the first and second jaw members between the spaced-apart and approximated positions.

In another aspect of the present disclosure, at least one of the first and second jaw members is adapted to connect to a source of energy for treating tissue grasped therebetween. In such aspects, an energy activation assembly disposed on the housing may also be provided. The energy activation assembly includes a switch configured to supply energy to the first and/or second jaw members. Further, the movable handle may be movable relative to the housing between an initial position, a compressed position, and an activated position.

The second leg of the torsion spring is configured to remain in fixed position in response to movement of the movable handle between the compressed and activated positions and, in the activated position, at least a portion of the handle is configured to contact the energy activation assembly to activate the switch.

In still another aspect of the present disclosure, the second leg is configured to translate in cooperation with the first leg in response to movement of the movable handle between the initial and compressed positions for applying an appropriate closure force to tissue grasped therebetween in the compressed position. Further, the appropriate closure pressure may be maintained, e.g., via tensioning of the torsion spring, during movement of the movable handle between the compressed and activated positions.

In yet another aspect of the present disclosure, the torsion spring is pre-loaded to a less-tensioned state and wherein, in response to longitudinal movement of the first leg when the force acting on the drive member is equal to or exceeds the threshold force, the torsion spring is further tensioned to a more-tensioned state.

Another surgical instrument provided in accordance with aspects of the present disclosure includes a movable handle, a drive member, a torsion spring, and a slider. The torsion spring includes a body, a first leg, and a second leg. The second leg of the torsion spring is engaged to the drive member. The slider includes a housing and a mandrel. The housing includes a post rotatably supporting the body of the torsion spring thereon. The housing is configured to permit movement of the second leg of the torsion spring relative to the housing. The mandrel extends from the housing and is operably coupled to the movable handle such that movement of the movable handle longitudinally translates the slider. When a force acting on the drive member is less than a threshold force, the slider and the second leg of the torsion spring are configured to translate longitudinally through the housing in cooperation with one another in response to movement of the movable handle, thereby transferring longitudinal movement of the slider into longitudinal movement of the drive member. When the force acting on the drive member is equal to or exceeds the threshold force, the torsion spring is tensioned in response to movement of the movable handle such that the second leg of the torsion spring and the drive member remain in fixed position during longitudinal movement of the slider.

In an aspect of the present disclosure, the surgical instrument further includes an end effector assembly operably coupled to the drive member. In such aspects, the drive member is configured to translate relative to the end effector assembly to actuate the end effector assembly.

In another aspect of the present disclosure, the end effector assembly includes first and second jaw members. At least one of the first and second jaw members is movable relative to the other between a spaced-apart position and an approximated position for grasping tissue therebetween in response to translation of the drive member relative to the end effector assembly.

In still another aspect of the present disclosure, the force acting on the drive member corresponds to a closure pressure applied to tissue grasped between the first and second jaw members.

In yet another aspect of the present disclosure, the movable handle is movable relative to the housing between an initial position, a compressed position, and an activated position. In such aspects, the slider and the second leg of the torsion spring are configured to translate longitudinally through the housing in cooperation with one another in response to movement of the movable handle between the initial and compressed positions. The second leg of the torsion spring and the drive member remain in fixed position during longitudinal movement of the slider in response to movement of the movable handle between the compressed and activated positions.

In still yet another aspect of the present disclosure, at least one of the first and second jaw members is adapted to connect to a source of energy for treating tissue grasped between the first and second jaw members. In such aspects, energy may be supplied to the at least one of the first and second jaw members in response to movement of the movable handle to the activated position.

In an aspect of the present disclosure, the housing retains the first end of the torsion spring in fixed relation relative to the housing. Alternatively, the first leg of the torsion spring may be operably positioned to bias the drive member in a longitudinal direction.

BRIEF DESCRIPTION OF THE DRAWINGS

Various aspects and features of the present disclosure described herein with reference to the drawings wherein:

FIG. 11A is a perspective view of another slider assembly provided in accordance with the present disclosure and configured for use with the surgical instrument of FIG. 1;

FIG. 12 is a rear, perspective, exploded view of the drive assembly, shaft, and end effector assembly of the surgical instrument of FIG. 1;

FIG. 15B' is an enlarged, side view of the distal ends of the jaw members of FIG. 15B;

FIG. 15C' is a top view of one of the jaw members of FIG. 15C;

FIG. 15D is a side view of the distal end of the surgical instrument of FIG. 1 incorporating still another configuration of jaw members provided in accordance with the present disclosure and disposed in the approximated position pressed against tissue to be spread and/or dissected;

FIG. 15D' is an enlarged, side view of the distal ends of the jaw members of FIG. 15D;

FIG. 16D is a side view of the jaw members of FIG. 15D disposed in the spaced-apart position spreading and/or dissecting tissue;

FIG. 19 is a side, perspective view of the distal end of the surgical instrument of FIG. 1 with the jaw members disposed in the spaced-apart position;

FIG. 20 is a side, perspective view of one of the jaw members of the surgical instrument of FIG. 1 with a portion thereof removed;

FIG. 21 is a transverse, cross-sectional view of the jaw member of FIG. 20;

FIG. 33 is a perspective view of the distal end of the drive and knife assemblies as shown in FIG. 29 and further including the jaw members disposed in the spaced-apart position;

FIG. 34 is a perspective view of the distal end of the drive and knife assemblies shown in FIG. 30 and further including the jaw members disposed in the approximated position;

FIG. 38 is a perspective view of the distal end of the drive and knife assemblies of the surgical instrument of FIG. 1 with the knife assembly disposed in an extended position;

FIG. 39 is a perspective view of the distal end of the drive and knife assemblies as shown in FIG. 38 and further including the jaw members disposed in the approximated position; and FIG. 40 is a top, cross-sectional view of the distal end of the drive and knife assemblies and including the jaw members, as shown in FIG. 39.

DETAILED DESCRIPTION

Figure 1:
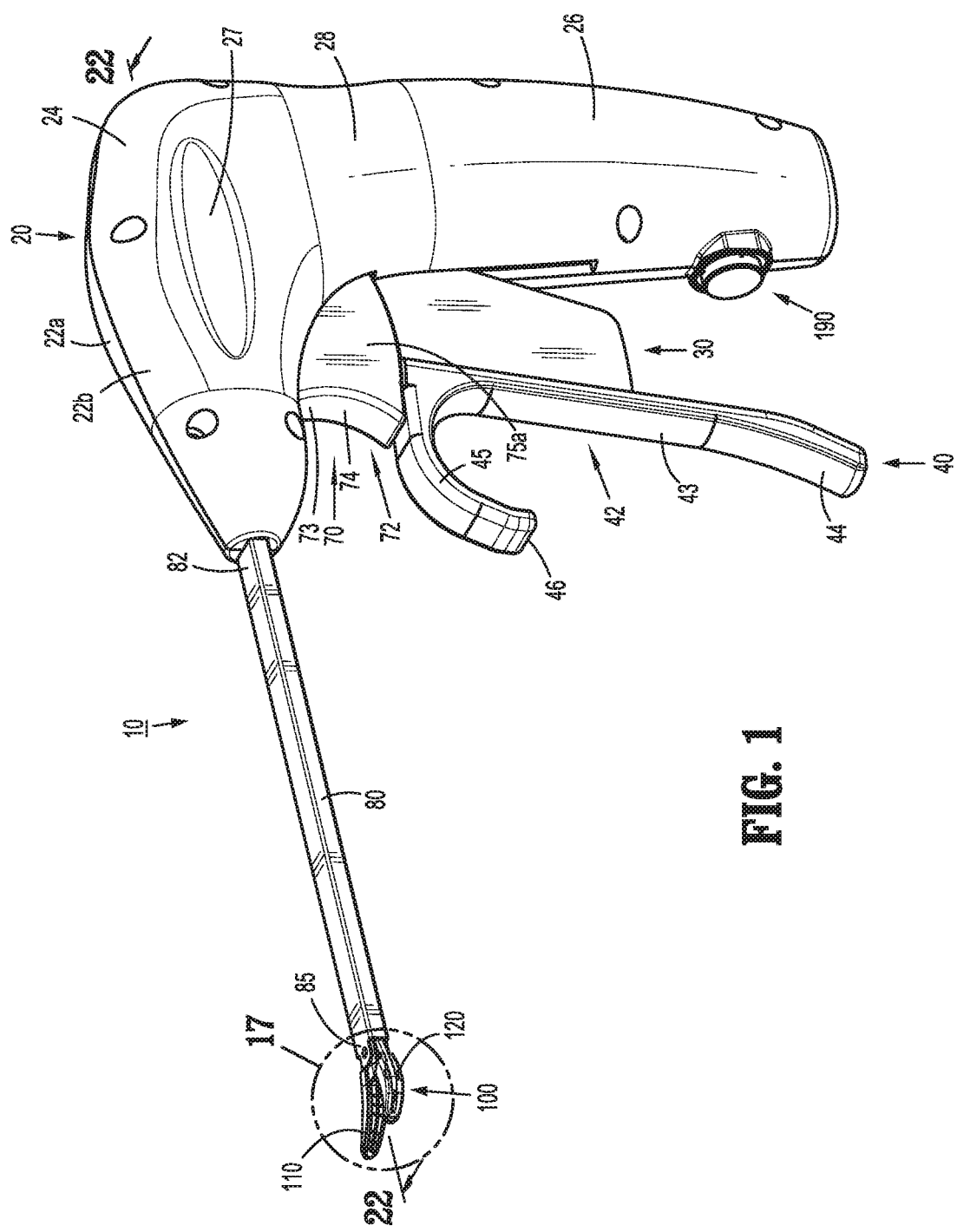
FIG. 1 is a perspective view of a surgical instrument provided in accordance with the present disclosure with jaw members of the end effector assembly of the surgical instrument disposed in a spaced-apart position.
Figure 2:
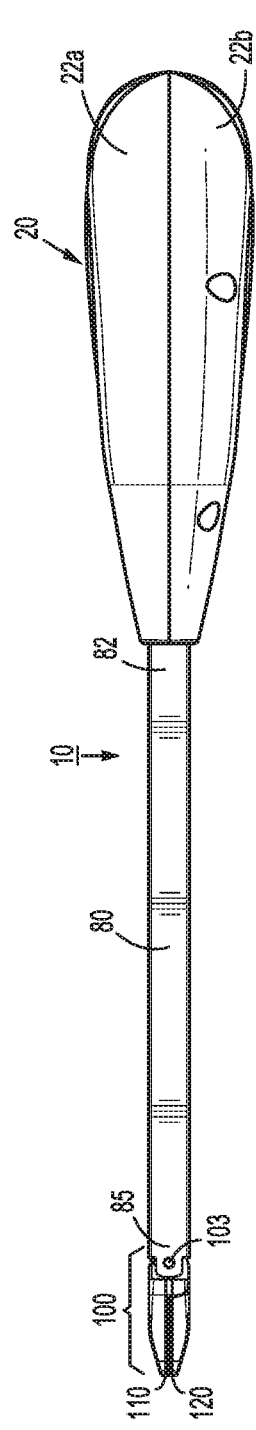
FIG. 2 is a top view of the surgical instrument of FIG. 1 with the jaw members disposed in an approximated position.
Figure 3:
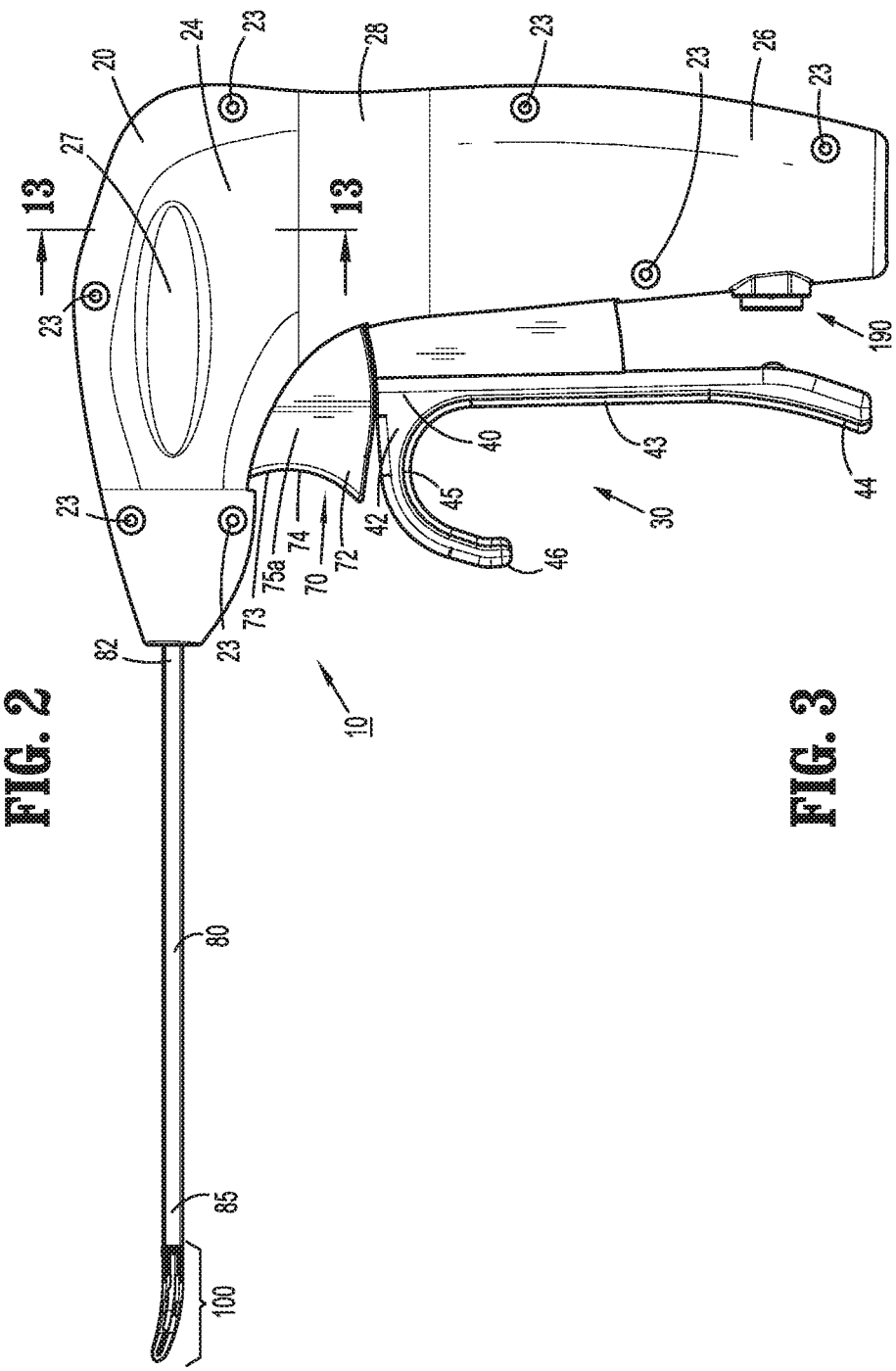
FIG. 3 is a side view of the surgical instrument of FIG. 1 with the jaw members disposed in the approximated position.

Referring generally to FIGS. 1-12, a surgical instrument provided in accordance with the present disclosure is shown generally identified by reference numeral 10. Instrument 10, as described below, is configured for grasping, treating, and/or dissecting tissue and may find particular applicability for use in performing tonsillectomy and/or adenoidectomy procedures, although use of instrument 10 in various other surgical procedures is also contemplated and within the scope of the present disclosure.

With reference to FIGS. 1, 7, 8, and 12, instrument 10 generally includes a housing 20, a handle assembly 30, a trigger assembly 70, a shaft 80, an end effector assembly 100, a drive assembly 140, a knife assembly 170, and an energy activation assembly 190. As detailed below, shaft 80 extends distally from housing 20 and supports end effector assembly 100 at distal end 85 thereof, drive assembly 140 operably couples handle assembly 30 with end effector assembly 100 to enable selective manipulation of jaw members 110, 120 of end effector assembly 100, knife assembly 170 is operably coupled with trigger assembly 70 to enable selective translation of a knife blade 174 of knife assembly 170 relative to end effector assembly 100, and energy activation assembly 190 enables energy to be selectively delivered to end effector assembly 100.

Instrument 10 may also include an electrosurgical cable (not shown) that connects instrument 10 to a generator (not shown) or other suitable power source, although instrument 10 may alternatively be configured as a battery-powered instrument. The electrosurgical cable includes lead wires, e.g., lead wires 107 (FIG. 12), extending therethrough that have sufficient length to extend through housing 20 and shaft 80 in order to operably couple the generator, energy activation assembly 190, and end effector assembly 100 with one another to enable the selective supply of energy to electrically-conductive plates 112, 122 of jaw members 110, 120 of end effector assembly 100, e.g., upon activation of activation switch 194 of energy activation assembly 190.

Referring to FIGS. 1-7, housing 20 houses the internal working components of instrument 10 and is formed from first and second housing components 22a, 22b configured to engage one another via a plurality of pin-aperture engagements 23 spaced around the perimeter of housing 20. Housing 20 defines a pistol-style configuration having a longitudinally-extending barrel portion 24 and a fixed handle portion 26 that extends from barrel portion 24 in generally perpendicular orientation relative thereto.

Housing 20, movable handle 40 of handle assembly 30, and trigger 72 of trigger assembly 70 are ergonomically configured to enable operable grasping of instrument 10 in a plurality of different positions. Housing 20, more specifically, defines an elongated indentation 27 within barrel portion 24 on either side thereof, while a waist 28 is recessed annularly about handle portion 26 adjacent the interconnection between handle portion 26 and barrel portion 24. Movable handle 40, more specifically, defines a grasping portion 42 having an elongated proximal leg 43 that extends the length of fixed handle portion 26 of housing 20, a proximal foot 44 disposed at the free end of proximal leg 43 and angled distally relative to proximal leg 43, and an arcuate segment 45 disposed at the opposite end of proximal leg 43 and extending distally therefrom. Arcuate segment 45 culminates in a distal tail 46 and defines a sufficient diameter so as to operably receive a user's finger between distal tail 46 and proximal leg 43. Trigger 72, more specifically, includes a concave trigger surface 73 defining a saddle 74 configured to help retain a user's finger therein.

Figure 4:
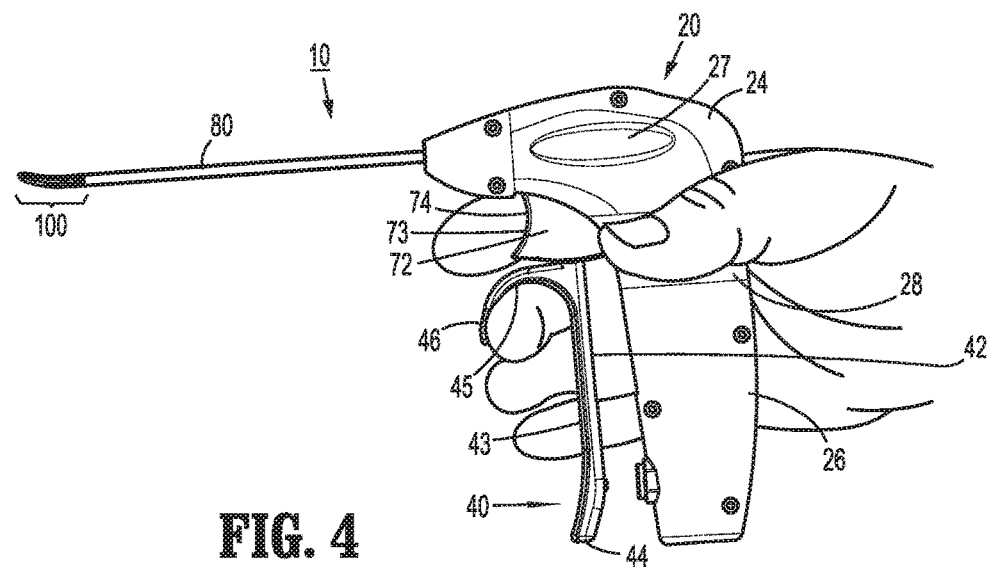
FIGS. 4-6 are side views of the surgical instrument of FIG. 1 illustrating various different configurations for operably grasping the surgical instrument.
Figure 5:
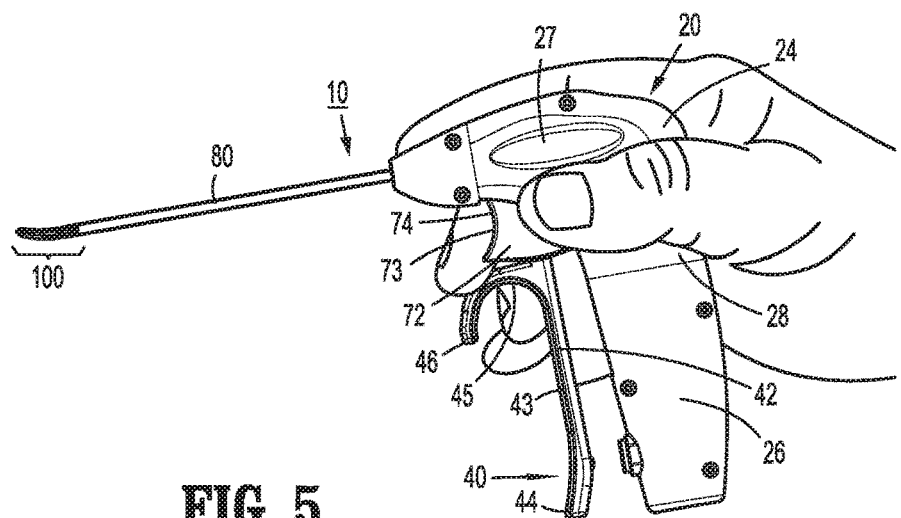
Figure 6:
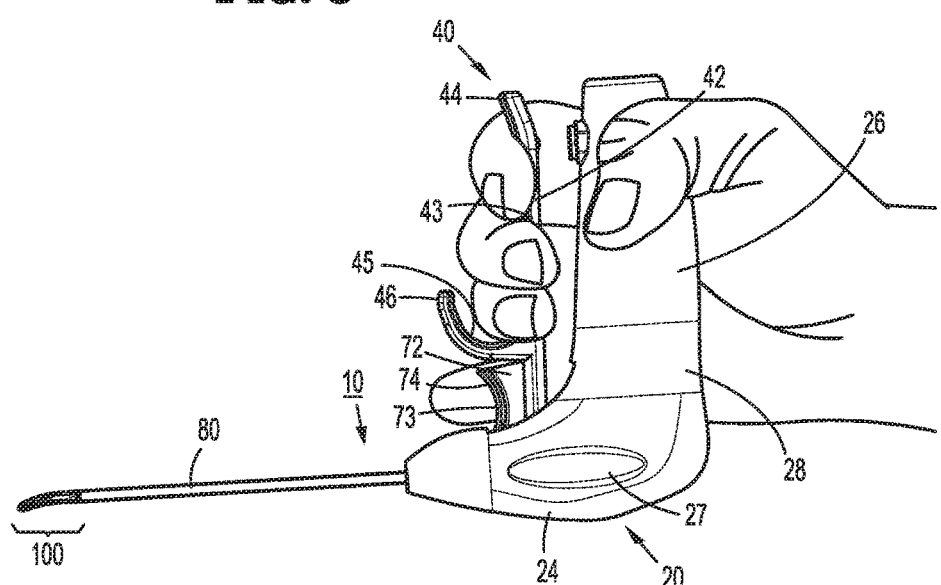

With particular reference to FIGS. 4-6, and initially to FIG. 4, in a first operable grasping position, the user's hand is positioned such that the thumb is partially received within waist 28, the tip of the index finger extends across trigger 72 and is partially received within saddle 74, the middle finger extends across movable handle 40 and is positioned adjacent arcuate segment 45 of movable handle 40 between proximal leg 43 and distal tail 46, and the ring finger and pinky are positioned distally of and adjacent to proximal leg 43. In this position, waist 28 inhibits slipping of the thumb, saddle 74 inhibits slipping of the index finger, proximal leg 43 and distal tail 46 retain the middle finger therebetween to enable both proximal and distal movement of movable handle 40, proximal leg 43 provides a surface against which the ring finger and pinky can be utilized to urge movable handle 40 proximally, and proximal foot 44 inhibits slipping of the ring finger and pinky off the free end of movable handle 40.

Referring to FIG. 5, in a second operable grasping position, the user's hand is positioned such that the index finger is partially received within elongated indentation 27 on the opposite side of housing 20, the middle finger extends transversely across trigger 72 and is partially received within saddle 74, the ring finger extends across movable handle 40 and is positioned adjacent arcuate segment 45 of movable handle 40 between proximal leg 43 and distal tail 46, and the pinky is positioned distally of and adjacent to proximal leg 43. In this position, elongated indentation 27 inhibits slipping of the index finger, saddle 74 inhibits slipping of the middle finger, proximal leg 43 and distal tail 46 retain the ring finger therebetween to enable both proximal and distal movement of movable handle 40, and proximal leg 43 provides a surface against which the pinky can be utilized to urge movable handle 40 proximally.

Referring to FIG. 6, in a third operable grasping position, the user's hand is positioned such that the thumb is wrapped around a free end of fixed handle portion 26 of housing 20, the index finger and middle finger are positioned proximally of and adjacent the free end of proximal leg 43 of movable handle 40, the ring finger extends across movable handle 40 and is positioned adjacent arcuate segment 45 of movable handle 40 between proximal leg 43 and distal tail 46, and the pinky extends across trigger 72 and is partially received within saddle 74. In this position, proximal foot 44 inhibits slipping of the index finger off the free end of movable handle 40, proximal leg 43 and distal tail 46 retain the ring finger therebetween to enable both proximal and distal movement of movable handle 40, proximal leg 43 provides a surface against which the index and middle fingers can be utilized to urge movable handle 40 proximally, and saddle 74 inhibits slipping of the pinky.

Figure 7:
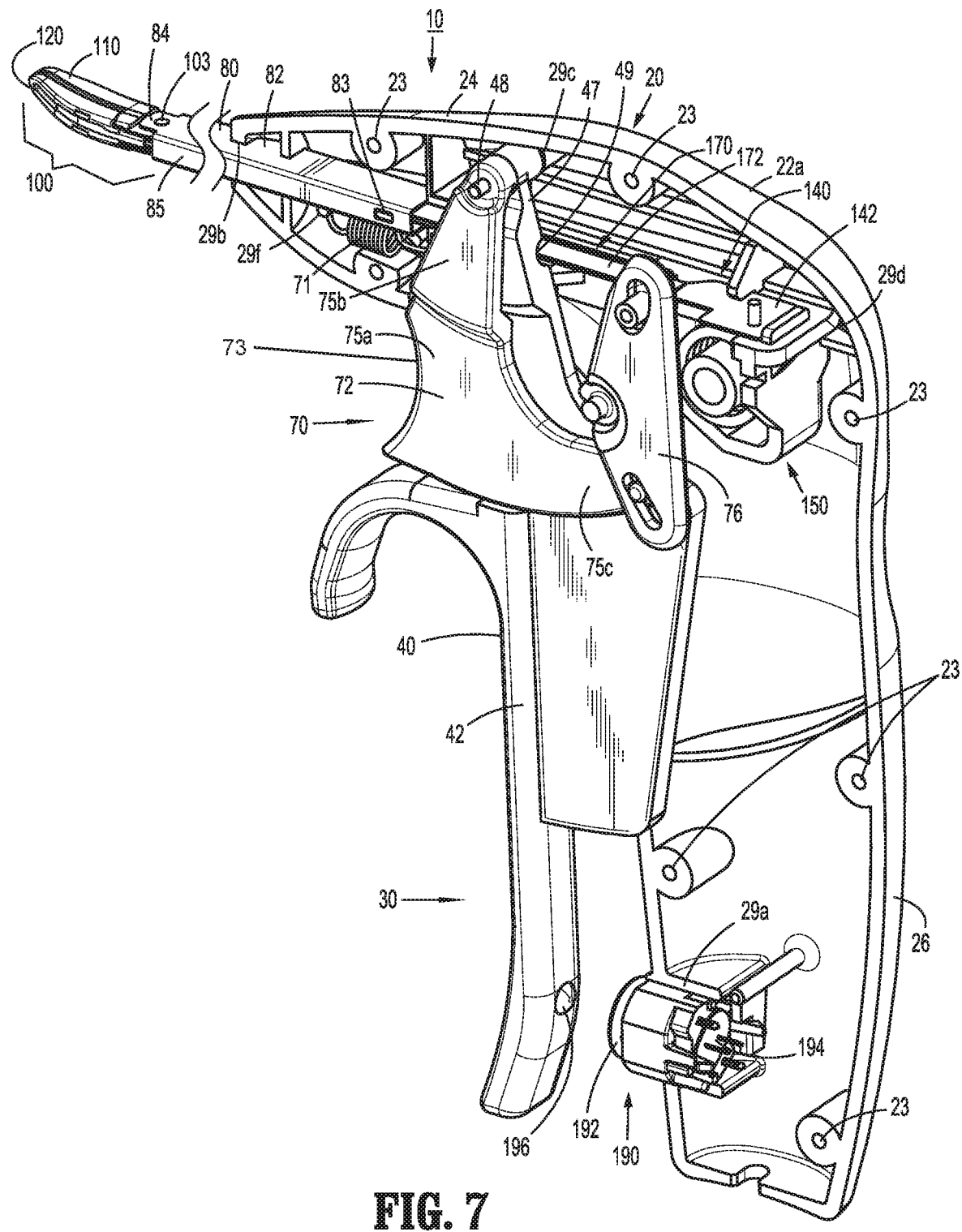
FIG. 7 is a rear, perspective view of the surgical instrument of FIG. 1 with the jaw members disposed in the approximated position and a portion of the housing removed to illustrate the internal components thereof.

With reference to FIG. 7, fixed handle portion 26 of housing 20 defines a bay 29a configured to receive and support energy activation assembly 190, which is operable to initiate and terminate the delivery of energy to end effector assembly 100. Energy activation assembly 190 includes a depressible button 192 that is mechanically coupled to a switch 194 mounted within bay 29a of fixed handle portion 26 and is engagable by a button activation post 196 extending proximally from a proximal side of movable handle 40 upon movement of the movable handle 40 to the activated position, as detailed below. Switch 194 is configured to electrically communicate with end effector assembly 100 and the generator (not shown) via suitable electrical wiring, e.g., leads 107 (FIG. 12), extending through housing 20, shaft 80, and/or an external cable (not shown) to enable energy to be supplied from the generator (not shown) to end effector assembly 100 upon activation of switch 194.

Figure 8:
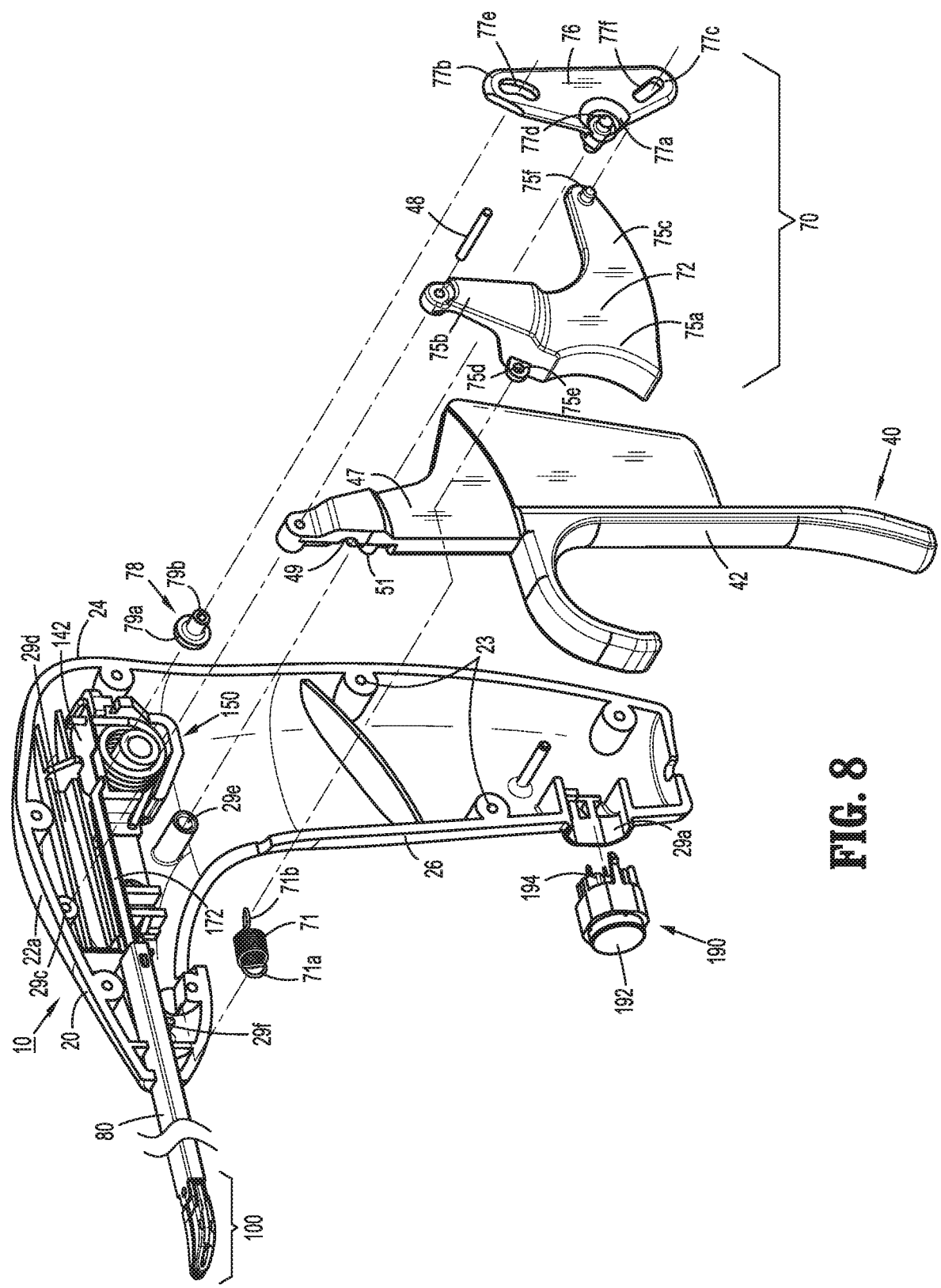
FIG. 8 is a front, perspective, partially-exploded view of the surgical instrument of FIG. 1 with the jaw members disposed in the approximated position and a portion of the housing removed to illustrate the internal components thereof.

Referring additionally to FIG. 8, barrel portion 24 of housing 20 defines a distal aperture 29b (FIG. 7) configured to receive proximal end 82 of shaft 80 therein, and an engagement feature (not shown) extending inwardly from each of first and second housing components 22a, 22b for receipt within opposed apertures 83 defined through proximal end 82 of shaft 80 for securing proximal end 82 of shaft 80 within barrel portion 24 of housing 20. Shaft 80 extends distally from housing 20 and defines a generally rectangular cross-sectional configuration oriented such that the larger width dimension thereof extends laterally and the smaller height dimension thereof extends vertically. This configuration of shaft 80 relative to the orientation of jaw members 110, 120 (FIG. 7) provides an enhanced "line-of-sight" for visualizing the surgical site adjacent end effector assembly 100. As described in greater detail below, shaft 80 includes a pair of spaced-apart clevis members 84 extending from the top and bottom walls, e.g., the larger width dimension walls, of shaft 80 at distal end 85 thereof, each of which defines an aperture 86 for receiving a pivot pin 103 to operably support end effector assembly 100 at distal end 85 of shaft 80. In this configuration, apertures 86 are vertically-aligned with one another. Shaft 80 further includes, as noted above, opposed apertures 83 defined through the side walls, e.g., the smaller height dimension walls, of shaft 80 at proximal end 82 thereof for receiving engagement features (not shown) extending inwardly from first and second housing components 22a, 22b to secure proximal end 82 of shaft 80 within housing 20.

Figure 13:
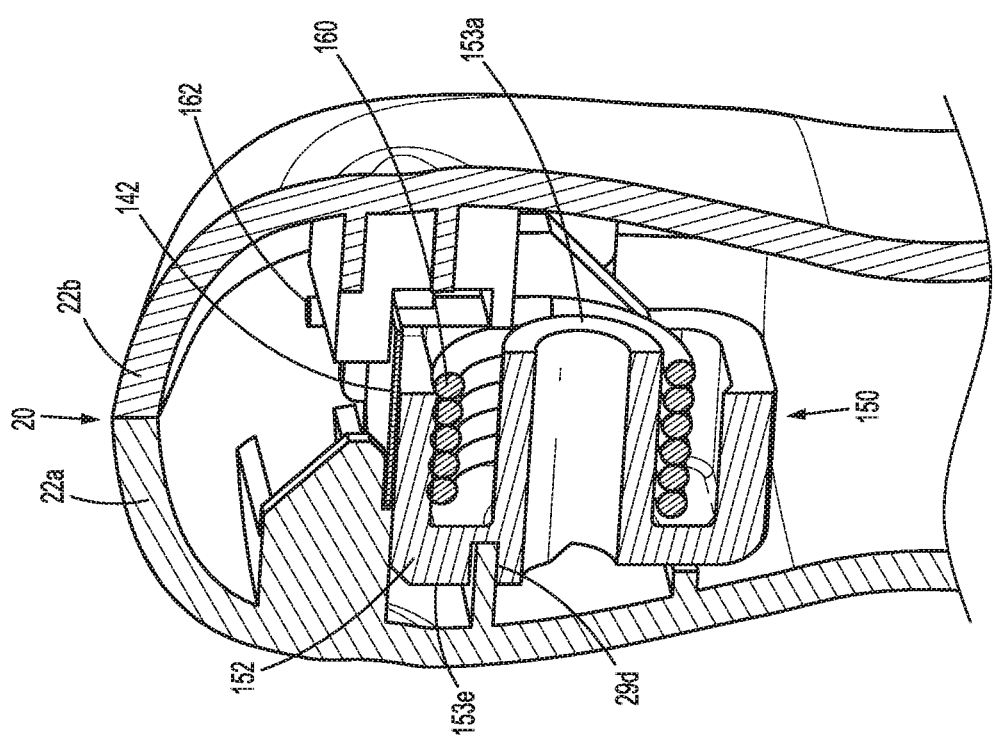
FIG. 13 is a transverse, cross-sectional view taken along section line "13-13" of FIG. 3.

Barrel portion 24 of housing further includes a pair of pivot apertures 29c, a longitudinal track 29d (FIG. 13), a pivot boss 29e, and a retention pin 29f. Each pivot aperture 29c is defined on the inwardly-facing surface of one of first and second housing components 22a, 22b (only pivot aperture 29c of first housing component 22a is shown) and is configured to receive pivot pin 48 to pivotably couple movable handle 40 and trigger 72 to housing 20. Longitudinal track 29d (FIG. 13) is defined on the inwardly-facing surface of first housing component 22a and is configured to guide translation of drive assembly 140 relative to housing 20. Pivot boss 29e extends inwardly from first housing component 22a and is configured to pivotably couple linkage 76 of trigger assembly 70 to housing 20. Retention pin 29f extends inwardly from first housing component 22a and is configured to retain a fixed end 71a of biasing member 71 of trigger assembly 70 in fixed position relative to housing 20. The importance of these features of barrel portion 24 of housing 20 will become more apparent in view of the description below.

Turning to FIGS. 7-13, handle assembly 30 includes a movable handle 40 that is movable relative to fixed handle portion 26 of housing 20 between an initial position, a compressed position, and an activated position, as explained in greater detail below, to impart movement of jaw members 110, 120 of end effector assembly 100 between a spaced-apart position and an approximated position for grasping tissue therebetween and for initiating the supply of energy to end effector assembly 100 for treating grasped tissue. Movable handle 40 includes grasping portion 42, detailed above, which extends from housing 20 adjacent fixed handle portion 26, and flange portion 47, which extends upwardly into housing 20. Flange portion 47 is pivotably coupled within housing 20 at the free end of flange portion 47 via pivot pin 48. Pivot pin 48 is engaged within and extends between pivot apertures 29c of first and second housing components 22a, 22b of housing 20 to permit movable handle 40 to pivot about pivot pin 48 and relative to housing 20 between the initial position, the compressed position, and the activated position. Pivot pin 48 is disposed on one side of, e.g., above, drive assembly 140, while grasping portion 42 of movable handle 40 is disposed on the other side of, e.g., below, drive assembly 140, to provide a mechanical advantage when actuating movable handle 40.

Flange portion 47 of movable handle 40 further includes a cut-out 49 defined therein and an engagement bulge 51 protruding therefrom. Cut-out 49 is configured to slidably receive drive plate 142 of drive assembly 140 and knife plate 172 of knife assembly 170. Engagement bulge 51 is configured to operably engage flange portion 47 of movable handle 40 with slider assembly 150 of drive assembly 140, as detailed below.

Drive assembly 140 includes drive plate 142 and slider assembly 150. Drive plate 142 extends distally from housing 20 and through shaft 80 to operably engage end effector assembly 100 such that, as detailed below, translation of drive plate 142 through shaft 80 and relative to end effector assembly 100 pivots jaw members 110, 120 of end effector assembly 100 between the spaced-apart and approximated positions. Slider assembly 150 operably couples flange portion 47 of movable handle 40 with drive plate 142 such that pivoting of movable handle 40 between the initial position and the compressed position pivots jaw members 110, 120 of end effector assembly 100 between the spaced-apart and approximated positions, while ensuring application of an appropriate closure force or closure force within an appropriate closure force range to tissue grasped between jaw members 110, 120 in the approximated position thereof.

Slider assembly 150 includes a proximal housing 152, a distal extension 154 extending distally from proximal housing 152, and a mandrel 156 disposed at the distal end of distal extension 154. Proximal housing 152 includes a post 153a configured to receive a torsion spring 160 thereabout, a first slot 153b configured to retain a first leg 161 of torsion spring 160 therein in fixed relation relative thereto, and a second slot 153c configured to operably receive second leg 162 of torsion spring 160 therein. Proximal housing 152 further includes an abutment rib 153d disposed thereon adjacent second slot 153c, and a flange member 153e configured for receipt within longitudinal track 29d (FIG. 13) of first housing component 22a of housing 20.

Figure 11:
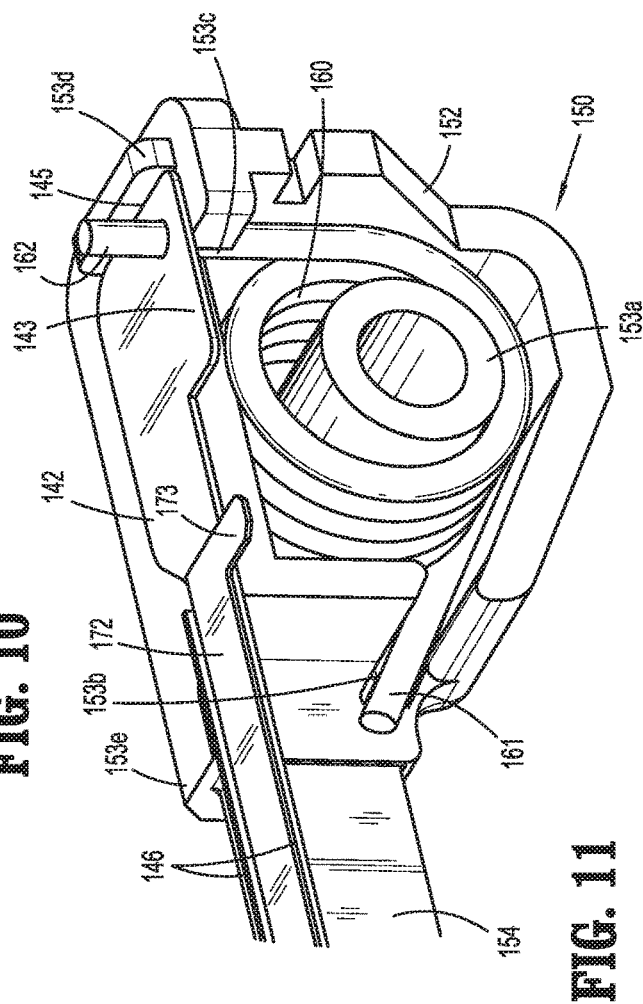
FIG. 11 is an enlarged, perspective view of the area of detail indicated as "11" in FIG. 10.
Figure 14:
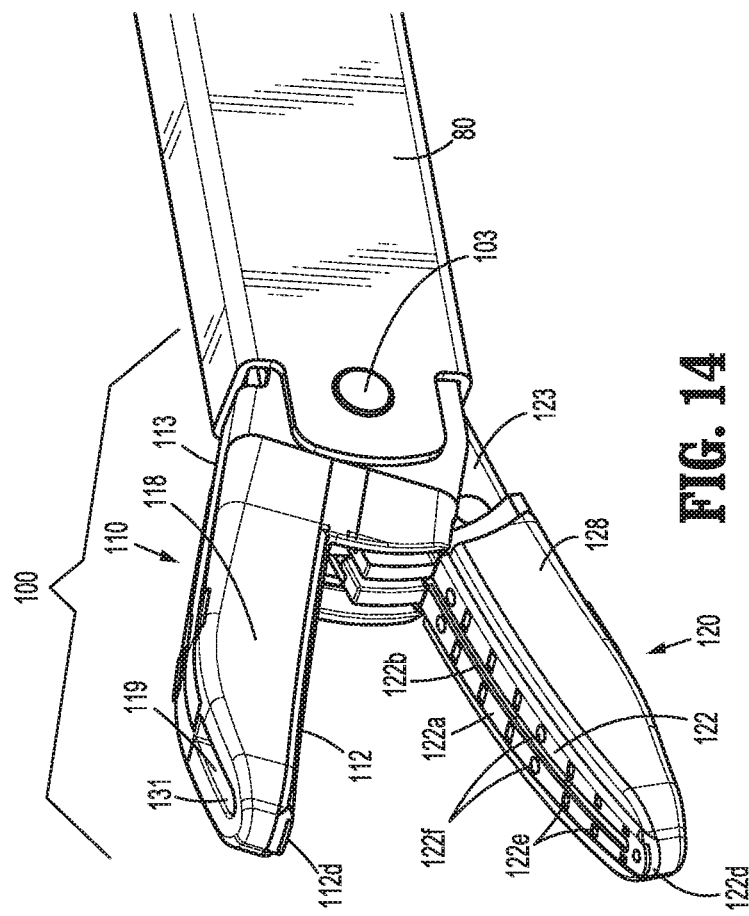
FIG. 14 is an enlarged, perspective view of the distal end of the surgical instrument of FIG. 1.

Referring briefly to FIG. 11A, another slider assembly 2150 provided in accordance with the present disclosure is similar to slider assembly 150 (FIGS. 10-11) except for the configuration of the proximal housing and spring; thus, only these differences are detailed below. Proximal housing 2152 of slider assembly 2150 is configured to house a compression spring 2160 therein. Compression spring 2160 defines a first end 2161 and a second end 2162. First end 2161 of compression spring 2160 is engaged with a vertical plate. Second end 2162 of compression spring 2160 is engaged with an inner wall of proximal housing 2152. In use, compression spring 2160 functions similar to torsion spring 160 (FIGS. 10-11), as detailed below, except that, rather than being further tensioned via application of a torsional force thereto, compression spring 2160 is further tensioned via application of a compressive force thereto.

Returning to FIGS. 7-13, mandrel 156, as noted above, is disposed at the distal end of distal extension 154 of slider assembly 150. Mandrel 156 includes a pair of spaced-apart walls 157 defining a channel 158 therebetween. Channel 158 is configured to receive engagement bulge 51 of flange portion 47 of movable handle 40 while permitting vertical sliding of engagement bulge 51 within channel 158. As a result of this configuration, upon pivoting of movable handle 40 between the initial, compressed, and activated positions, engagement bulge 51 is urged into contact with one of the walls 157 defining channel 158 to thereby translate slider assembly 150 within housing 20. The vertical sliding of engagement bulge 51 within channel 158 during such urging ensures that slider assembly 150 is translated longitudinally within and relative to housing 20 despite the arcuate travel of movable handle 40 as movable handle is pivoted about pivot pin 48 relative to housing 20.

Drive plate 142 includes a flange 143 disposed at the proximal end thereof. Flange 143 defines an aperture 144 configured to receive second leg 162 of torsion spring 160 therein such that translation of second leg 162 of torsion spring 160 relative to housing 20 effects corresponding translation of drive plate 142 relative to housing 20. With respect to slider assembly 2150, vertical plate 2163 is engaged within a slot 2144 defined within drive plate 142 (see FIG. 11A), and functions in a similar manner as detailed below with respect to slider assembly 150. Flange 143 further defines a proximal edge 145 configured to abut abutment rib 153d of proximal housing 152 in a proximal-most position of drive plate 142 relative to slider assembly 150 to inhibit further proximal movement of drive plate 142 relative to slider assembly 150.

Drive plate 142, as mentioned above, extends distally from housing 20 and through shaft 80 to operably engage end effector assembly 100. Drive plate 142 is oriented similarly to shaft 80, e.g., such that the width of drive plate 142 extends along the width dimension of shaft 80. Drive plate 142 further defines a track edge 146 extending along a portion of each longitudinal side thereof. Track edges 146 are configured to slidably receive knife plate 172, as detailed below. A cam-pin aperture 147 configured to receive a cam pin 105 associated with end effector assembly 100 is defined transversely through drive plate 142 towards the distal end of drive plate 142. A mouth 149 configured to receive a pivot pin 103 associated with end effector assembly 100 is defined at the distal end of drive plate 142.

Figure 9:
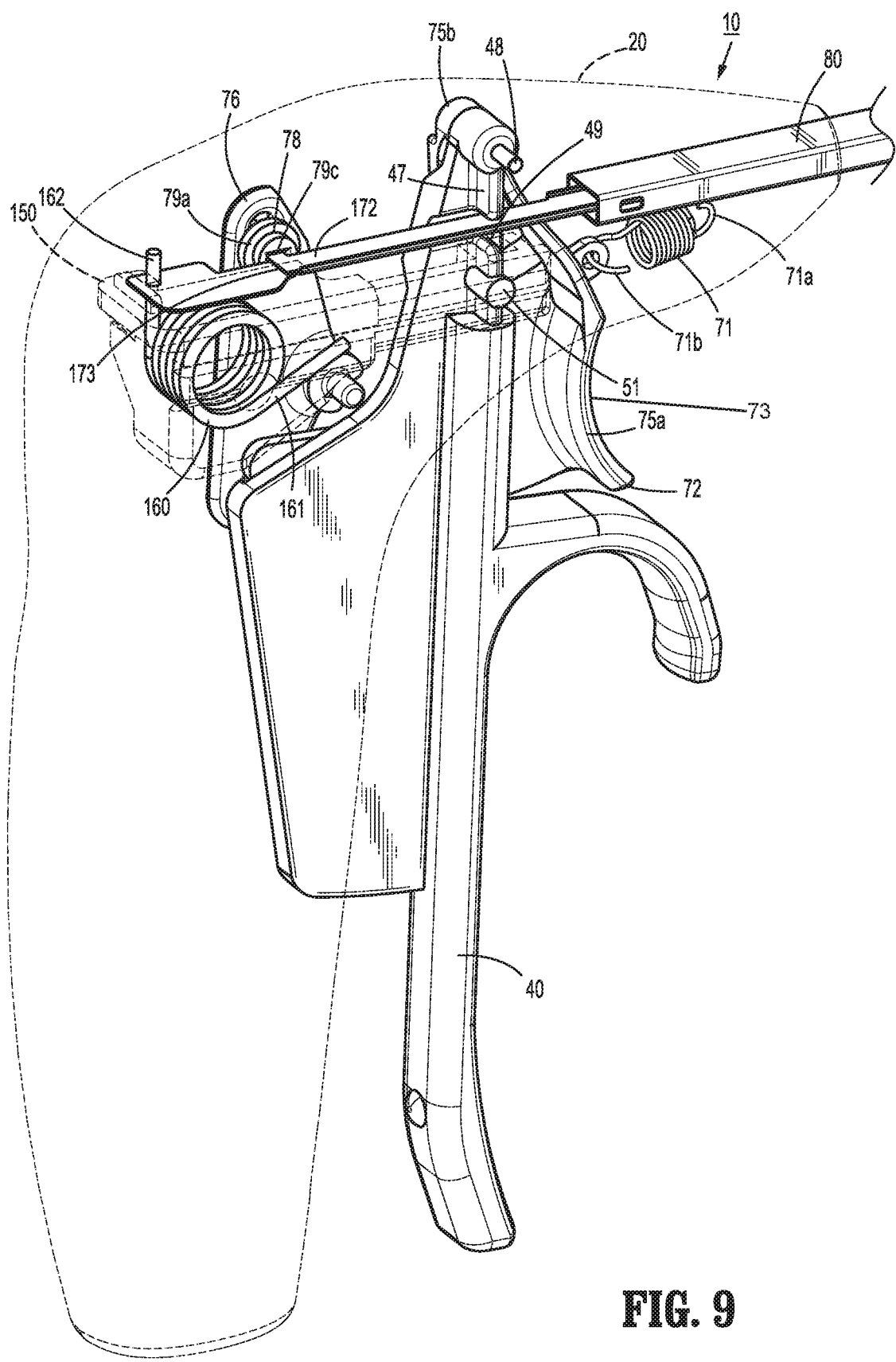
FIG. 9 is a rear, perspective view of the handle, trigger, and drive assemblies of the surgical instrument of FIG. 1 with a movable handle of the handle assembly disposed in an initial position and a trigger of the trigger assembly disposed in an un-actuated position.
Figure 9A:
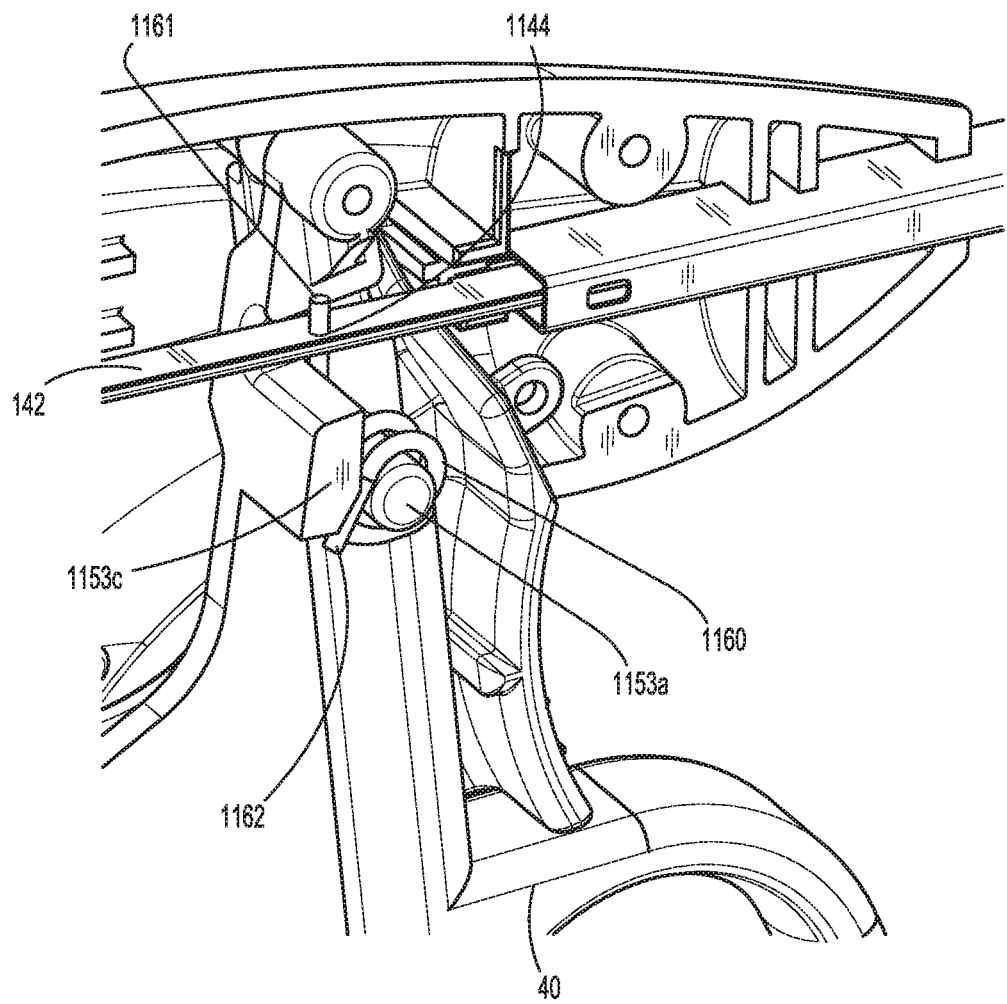
FIG. 9A is a rear, perspective view of a portion of the proximal end of the surgical instrument of FIG. 1 incorporating another configuration of a drive assembly provided in accordance with the present disclosure.
Figure 10:
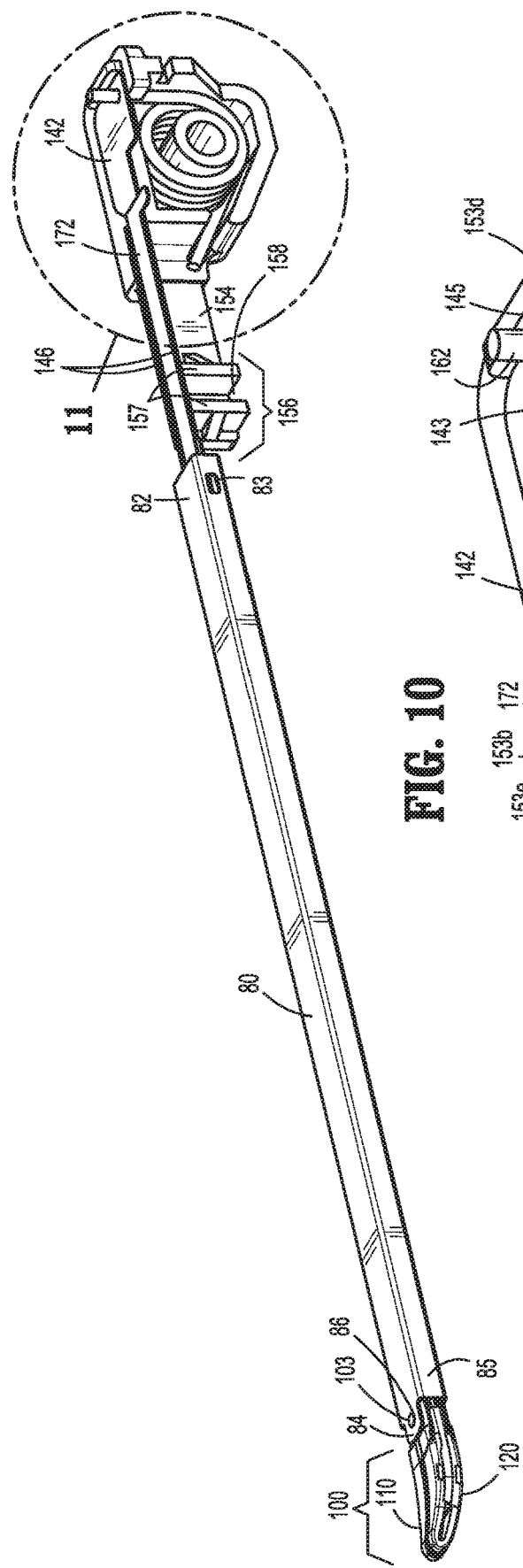
FIG. 10 is a front, perspective view of the drive assembly, shaft, and end effector assembly of the surgical instrument of FIG. 1.

With momentary reference to FIG. 9A, as an alternative to providing a slider assembly that operably retains a torsion spring therein for coupling to drive plate 142, a torsion spring 1160 may be operably coupled between movable handle 40 and drive plate 142 without a slider assembly. More specifically, in some embodiments, torsion spring 1160 is mounted about a post 1153a extending transversely from movable handle 40 and includes a first leg 1161 and a second leg 1162. First leg 1161 of torsion spring 1160 is configured for receipt within an aperture 1144 defined through drive plate 142 to operably couple movable handle 40 with drive plate 142, while second leg 1162 of torsion spring 1160 is fixed relative to movable handle 40 via abutment with a protrusion 1153c thereof. In use, torsion spring 1160 operates similarly to torsion spring 160 (FIGS. 10-11) and, thus, a separate description of the use of torsion spring 1160 is omitted as being superfluous.

With reference to FIGS. 14-21, as mentioned above, end effector assembly 100 is operably supported at distal end 85 of shaft 80 and includes opposing jaw members 110, 120 pivotably coupled to one another and movable relative to one another and shaft 80 between a spaced-apart position and an approximated position for grasping tissue therebetween. Each jaw member 110, 120 includes an electrically-conductive plate 112, 122, a jaw frame 113, 123, a spacer 115 (only spacer 115 of jaw member 110 is shown (FIG. 21)), and an outer housing 118, 128, each of which is detailed below. Jaw members 110, 120 define curved configurations, wherein jaw members 110, 120 bend upwardly from a longitudinal axis of shaft 80, e.g., towards the upper, larger width dimension wall of shaft 80. This configuration facilitates use of instrument 10 in tonsillectomy and adenoidectomy procedures as well as other surgical procedures and allows for increased visualization of the surgical site in these and other procedures. Except where specifically noted otherwise, jaw members 110, 120 define mirror-image configurations of one another.

Jaw frames 113, 123 of jaw members 110, 120 each include a pair of spaced-apart proximal flanges 113a, 123a and a distal jaw support 113b, 123b. Jaw frames 113, 123 are formed via stamping and made from stainless steel, although other manufacturing processes and/or materials for forming jaw frames 113, 123 are also contemplated. Proximal flanges 113a of jaw member 110 are spaced-apart further than proximal flanges 123a of jaw member 120 so as to allow proximal flanges 123a of jaw member 120 to be positioned between proximal flanges 113a of jaw member 110 during assembly. Further, the proximal flanges 113a, 123a of each pair define aligned pivot apertures 114a, 124a and aligned cam slots 114b, 124b. Pivot pin 103 of end effector assembly 100 is configured for vertical insertion through apertures 86 of clevis members 84 of shaft 80 and pivot apertures 114a, 124a to pivotably couple jaw members 110, 120 to shaft 80 and one another with jaw members 110, 120 being laterally movable, e.g., along the larger width dimension of shaft 80, between the spaced-apart and approximated positions. Pivot pin 103 is configured to at least partially enter mouth 149 of drive plate 142 to permit drive plate 142 to slide further distally relative to end effector assembly 100 to a position wherein mouth 149 of drive plate 142 at least partially surrounds pivot pin 103.

The cam slots 114b of proximal flanges 113a of jaw member 110 are oppositely angled relative to the cam slots 124b of proximal flanges 123a of jaw member 120. Cam pin 105 of end effector assembly 100 is configured for insertion through each cam slot 114b, 124b as well as cam-pin aperture 147 of drive plate 142 to operable couple drive plate 142 with jaw members 110, 120 such that translation of drive plate 142 relative to jaw members 110, 120 pivots jaw members 110, 120 about pivot pin 103 and relative to one another and shaft 80 between the spaced-apart and approximated positions.

With particular reference to FIGS. 19-21, although only the features of jaw member 110 or jaw member 120 are described below and/or illustrated in the figures, it is noted that jaw members 110, 120 defines a mirror-image configurations of one another (unless specifically contradicted herein) and, thus, any description and/or illustration of one jaw member 110, 120 applies similarly to the other jaw member 110, 120.

Distal jaw support 113b of jaw frame 113 of jaw member 110 extends distally from proximal flange 113a and defines a generally "L-shaped" configuration. Distal jaw support 113b is configured to support electrically-conductive plate 112, spacer 115, and outer housing 118 of jaw member 110 thereon. However, distal jaw support 113b do not extend distally the entire length of jaw member 110. Rather, distal jaw support 113b defines a length of about 50% to about 75% of the lengths of electrically-conductive plate 112, spacer 115, and outer housing 118 such that about 25% to about 50% of the lengths of these components extend distally beyond distal jaw support 113b.

Spacer 115 of jaw member 110 defines a generally "M-shaped" configuration, is formed from an electrically-insulative material, and is overmolded onto distal jaw support 113b during a first overmold, although other manufacturing processes are also contemplated. Spacer 115 defines a body 116a and a pair of wings 116b surrounding body 116a. Spacer 115 is positioned to electrically-isolate electrically-conductive plate 112 and distal jaw support 113b from one another. A knife slot 116c extends longitudinally through body 116a of spaced 115 and is generally centered relative to body 116a. Knife slot 116c is open only to the top of spacer 115, except for the distal portion thereof, which extends beyond distal jaw support 113b and is open on both the top and bottom sides thereof to provide a window 116d. A support-receiving channel 116e extends longitudinally through body 116a at a position laterally offset relative to knife slot 116c so as to not interfere therewith. Support-receiving channel 116e is open to the bottom of spacer 115 and is configured to receive the upright of the "L-shaped" distal jaw support 113b upon the first overmolding of spacer 115 thereabout. Body 116a of spacer 115 further defines a tunnel 116f configured to permit passage of lead wire 107 therethrough.

The electrically-conductive plate 112, 122 of each jaw member 110, 120 defines a generally planar tissue-contacting surface 112a, 122a, an elongated slot 112b, 122b extending through the respective tissue-contacting surface 112a, 122a, a pair of legs 112c, 122c extending downwardly from each side of the respective tissue-contacting surface 112a, 122b, and a distal edge 112d, 122d disposed at the distal end of the respective tissue-contacting surface 112a, 122a. Electrically-conductive plates 112, 122 extend from the proximal heels of jaw members 110, 120, e.g., the interface between flanges 113a, 123a and the distal portions of jaw members 110, 120, to the distal tips of jaw members 110, 120. Jaw housing 118 of jaw member 110 includes a pair of proximal tissue stops that extend therefrom about either side of jaw member 120 such that, in conjunction with the positioning of electrically-conductive plates 112, 122 at the proximal heel of jaw members 110, 120, grasping of tissue proximally of electrically-conductive plates 112, 122 is inhibited.

Tissue-contacting surfaces 112a, 122a define a plurality of spaced-apart recesses 112e, 122e therein that facilitate grasping tissue. Tissue-contacting surface 112a of electrically-conductive plate 112 of jaw member 110 and/or tissue-contacting surface 122a of electrically-conductive plate 122 of jaw member 120 may further include a plurality of stop members 122f disposed thereon. Stop members 122f may be constructed of a heat-resistant ceramic deposited onto the tissue-contacting surfaces 112a, 122a, an electrically non-conductive plastic molded onto tissue-contacting surfaces 112a, 122a, an electrical conductive material isolated from the respective tissue-contacting surface 112a, 122a, or may be formed from and/or manufactured in any other suitable fashion.

Each wing 116b of spacer 115 of jaw member 110 defines a slot 116g, open at the top end thereof, that is configured for receiving one of the legs 112c of electrically-conductive plate 112. Wire 107, which extends through tunnel 116f defined within spacer 115 is configured to electrical connect to an underside of electrically-conductive plate 112 towards the distal end thereof for enabling the selective supply of energy thereto. Wire 107 is configured to extend proximally through shaft 80 and into housing 20, ultimately coupling to energy activation assembly 190 (FIG. 7) and/or extending through the cable (not shown) to couple to the generator (not shown).

Outer housings 118, 128 are formed about jaw members 110, 120 via a second overmold process, such that each outer housing 118, 128 partially encloses respective jaw members 110, 120 with the exception of a portion of the distal jaw support 113b, 123b thereof and the tissue-contacting surface 112a, 122a thereof, which remain exposed. Further, legs 112c, 122c of electrically-conductive plates 112, 122 of jaw members 110, 120 and the spacers 115 (only spacer 115 of jaw member 110 is shown) thereof each define a plurality of fill-apertures 122g (only fill-apertures 122g of electrically-conductive plate 122 of jaw member 120 are illustrated) that, upon overmolding of outer housings 118, 128 about respective jaw members 110, 120 are filled with the overmolded material forming outer housings 118, 128 to lock the components of each jaw member 110, 120 in an assembled condition. Further, outer housings 118, 128 define lengths extending along the sides of respective jaw members 110, 120 and thicknesses that decrease in the proximal-to-distal direction along the lengths thereof. Outer housings 118, 128 also define windows 119, 129 that align with and communicate with the windows 116d of the respective spacers 115 (only spacer 115 of jaw member 110 is illustrated) and the knife slots 112b, 122b of the respective electrically-conductive plate 112, 122 thereof so as to define an opening 131, 132 extending through the distal portion of each jaw member 110, 120 transversely relative to the plane defined by the respective tissue-contacting surface 112a, 122a.

Figure 15:
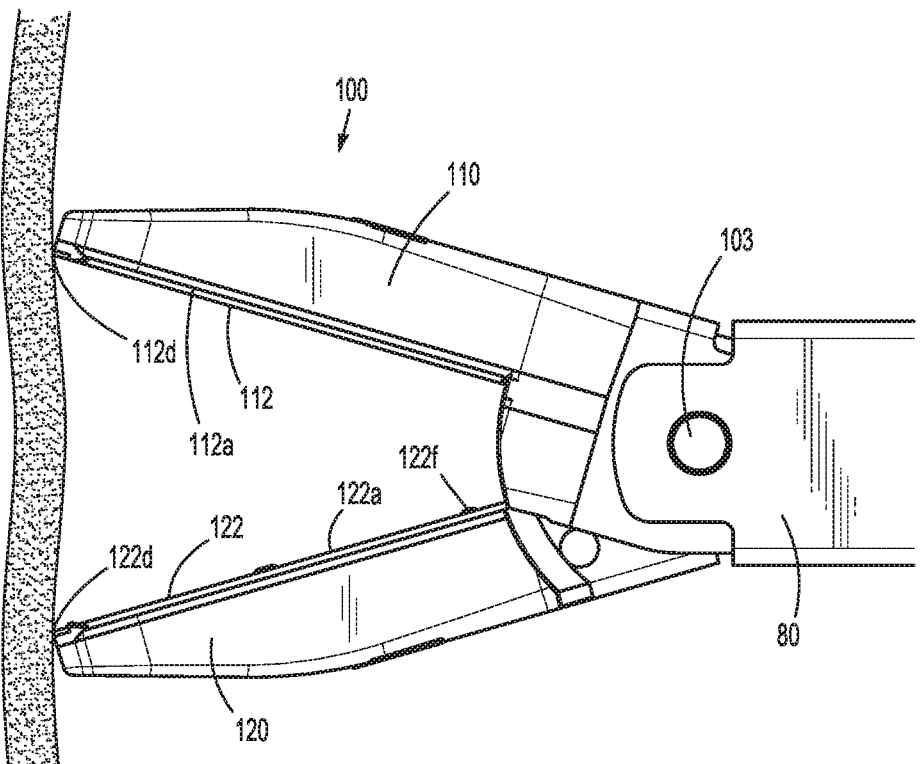
FIG. 15 is a side view of the distal end of the surgical instrument of FIG. 1 with the jaw members disposed in the spaced-apart position adjacent tissue to be grasped.
Figure 16:
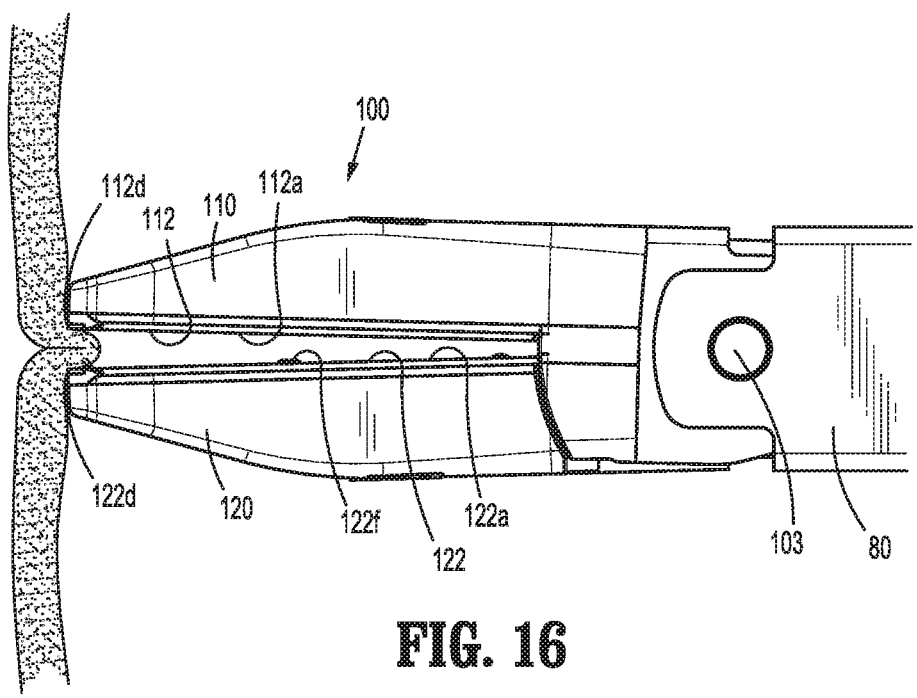
FIG. 16 is a side view of the distal end of the surgical instrument of FIG. 1 with the jaw members disposed in the approximated position grasping tissue at the distal ends thereof.

With outer housings 118, 128 formed about jaw members 110, 120, respectively, distal edges 112d, 122d of electrically-conductive plates 112, 122 overlap the distal ends of outer housings 118, 128 such that, as illustrated in FIGS. 15 and 16, distal edges 112d, 122d can be utilized to pinch tissue therebetween. In particular, this configuration enables pinching of planar tissue structures that lack substantial protruding portions that would otherwise enable grasping, such as the tissue wall illustrated in FIGS. 15 and 16.

Figure 15A:
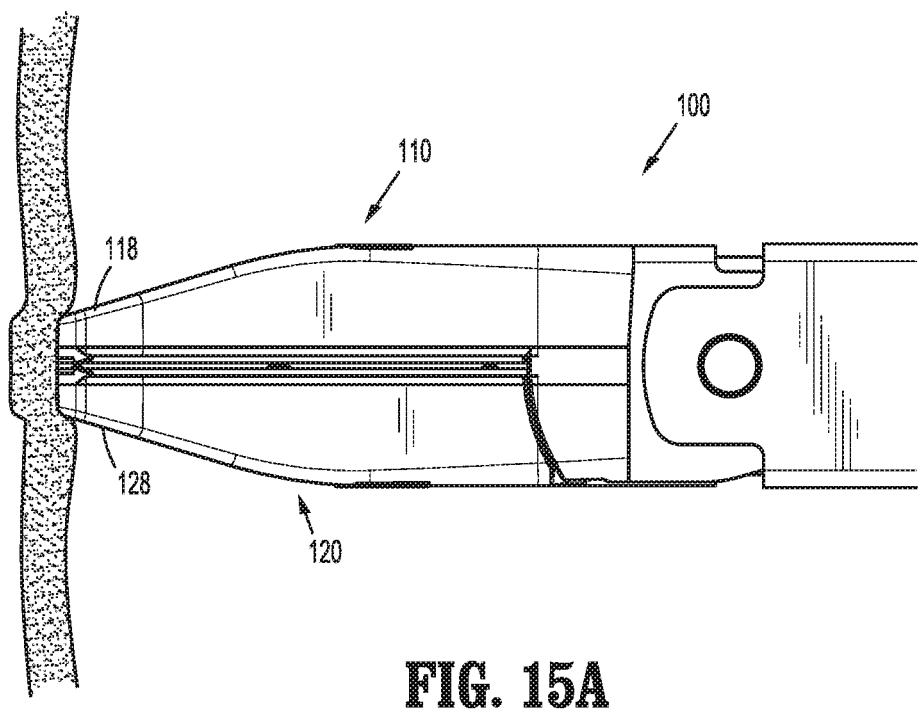
FIG. 15A is a side view of the distal end of the surgical instrument of FIG. 1 with the jaw members disposed in the approximated position pressed against tissue to be spread and/or dissected.
Figure 16A:
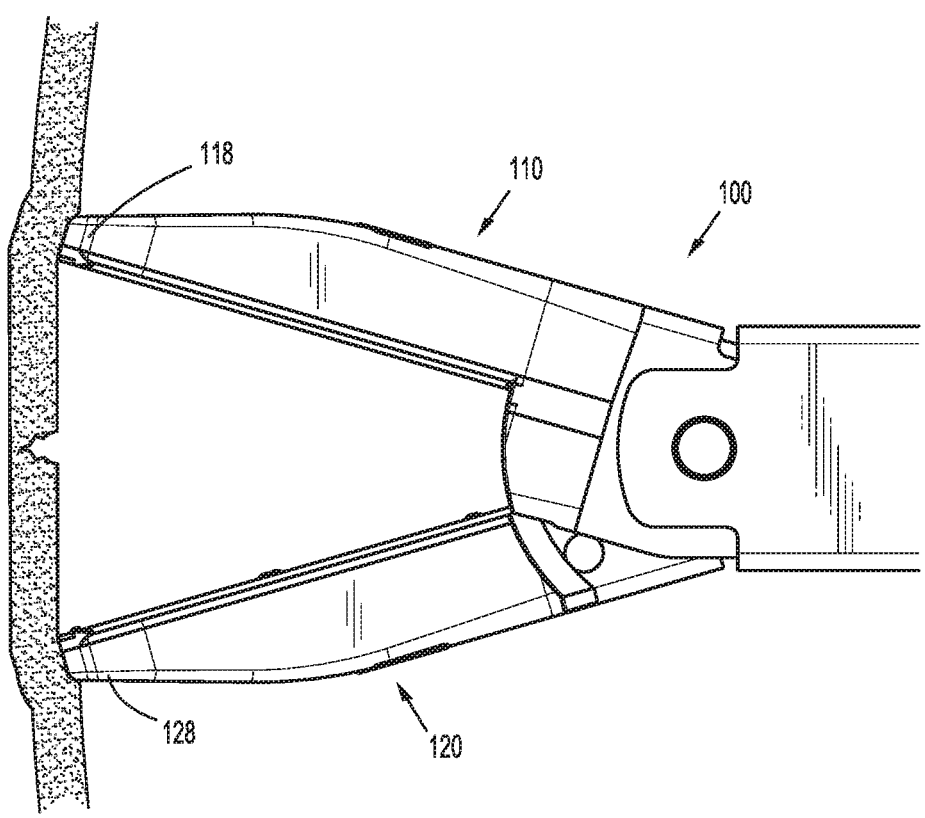
FIG. 16A is a side view of the distal end of the surgical instrument of FIG. 1 with the jaw members disposed in the spaced-apart position spreading and/or dissecting tissue.

Referring to FIGS. 15A and 16A, jaw members 110, 120 may further be utilized to spread and/or dissect tissue. In order to do so, with jaw members 110, 120 disposed in the approximated position, end effector assembly 100 may be manipulated such that the distal tips of jaw members 110, 120 are pressed into contact with tissue to be spread and/or dissected, as shown in FIG. 15A. Thereafter, jaw members 110, 120 are moved to the spaced-apart position such that the distal ends of outer housings 118, 128 of jaw members 110, 120, respectively, push tissue in opposite directions, thus spreading and/or dissecting tissue. Various configurations of the distal ends of outer housings 118, 128 of jaw members 110, 120 to further facilitate spreading and/or dissecting tissue are detailed below. As also detailed below, drive assembly 140 (FIG. 12) defines a pre-loaded configuration wherein drive assembly 140 (FIG. 12) is always under tension, such that backlash upon moving jaw members 110, 120 from the approximated position back to the spaced-apart position is eliminated. Such a configuration facilitates spreading and/or dissecting tissue by allowing for a more smooth and consistent transition of jaw members 110, 120 from the approximated position back to the spaced-apart position.

Figure 15B:
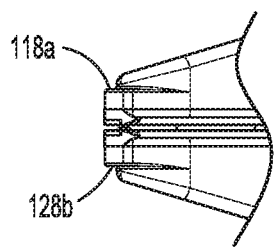
FIG. 15B is a side view of the distal end of the surgical instrument of FIG. 1 incorporating another configuration of jaw members provided in accordance with the present disclosure and disposed in the approximated position pressed against tissue to be spread and/or dissected.
Figure 15B:
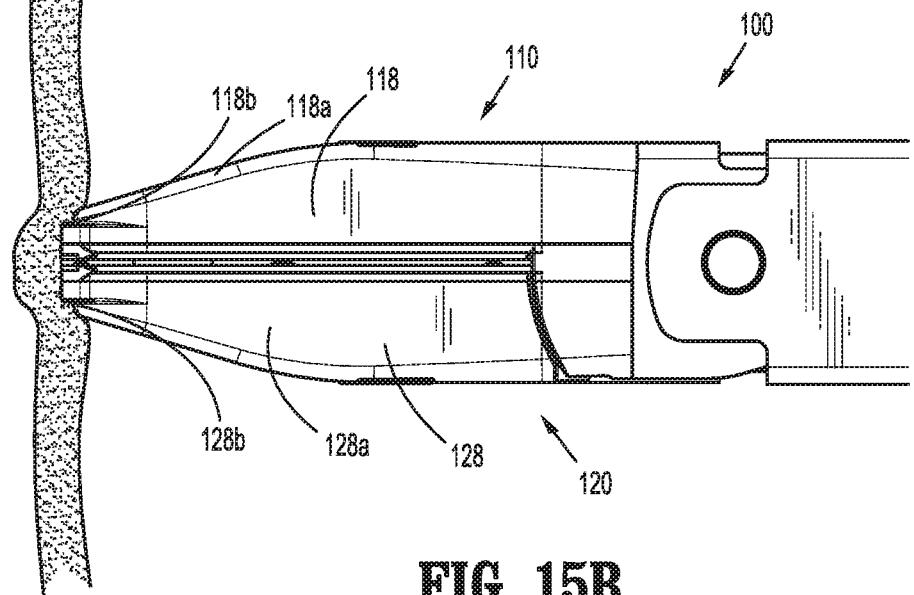
Figure 16B:
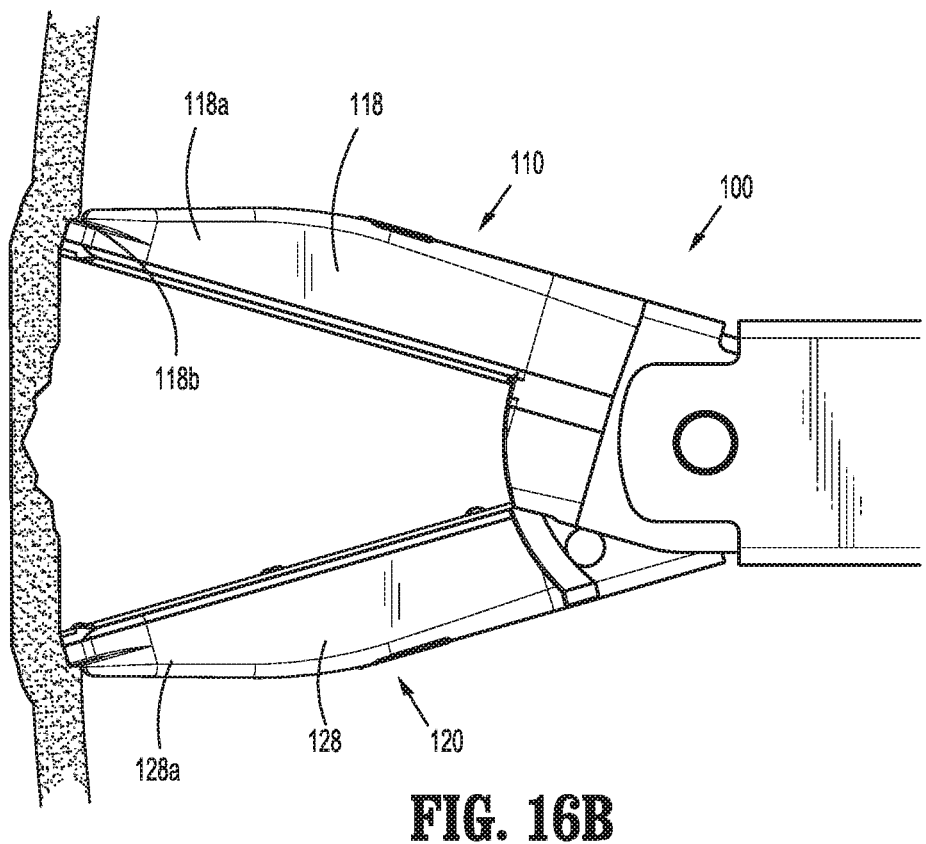
FIG. 16B is a side view of the jaw members of FIG. 15B disposed in the spaced-apart position spreading and/or dissecting tissue.

Turning to FIGS. 15B, 15B', and 16B, in some embodiments, the distal ends of outer housings 118, 128 of jaw members 110, 120 define cut-outs that form shelves 118b, 128b between the distal ends of outer housings 118, 128 and the body portions 118a, 128a of housings 118, 128, respectively. Shelves 118b, 128b, as shown in FIGS. 15B, 15B', and 16B facilitate the retention of tissue via the distal ends of outer housings 118, 128, thus inhibiting slipping of tissue and facilitating spreading and/or dissecting tissue.

Figure 15C:
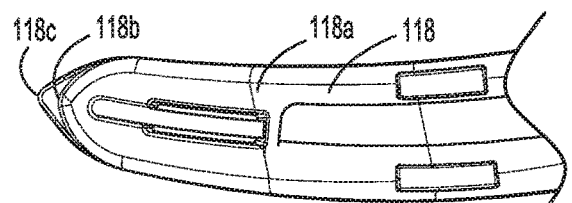
FIG. 15C is a side view of the distal end of the surgical instrument of FIG. 1 incorporating yet another configuration of jaw members provided in accordance with the present disclosure and disposed in the approximated position pressed against tissue to be spread and/or dissected.
Figure 15C:
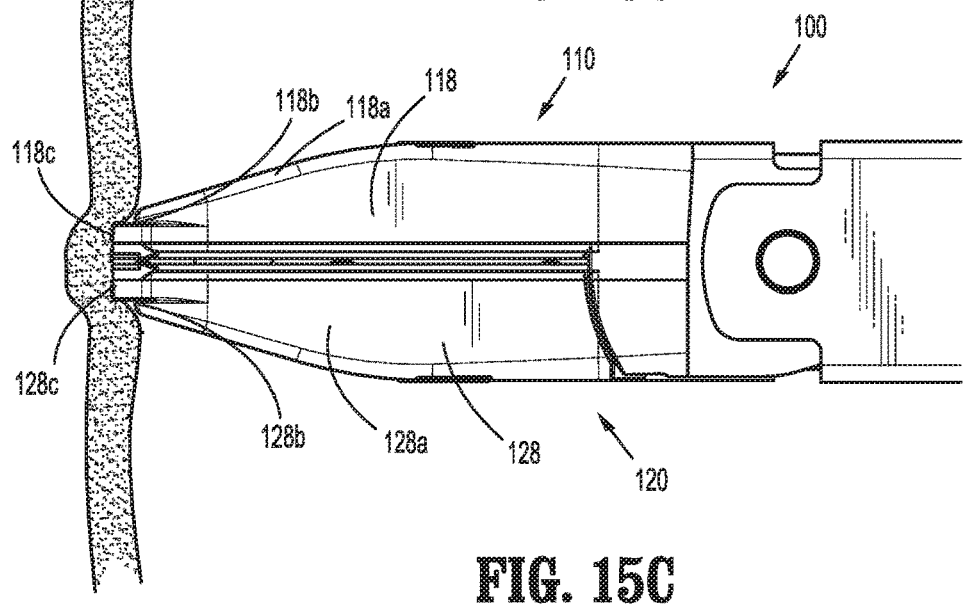
Figure 16C:
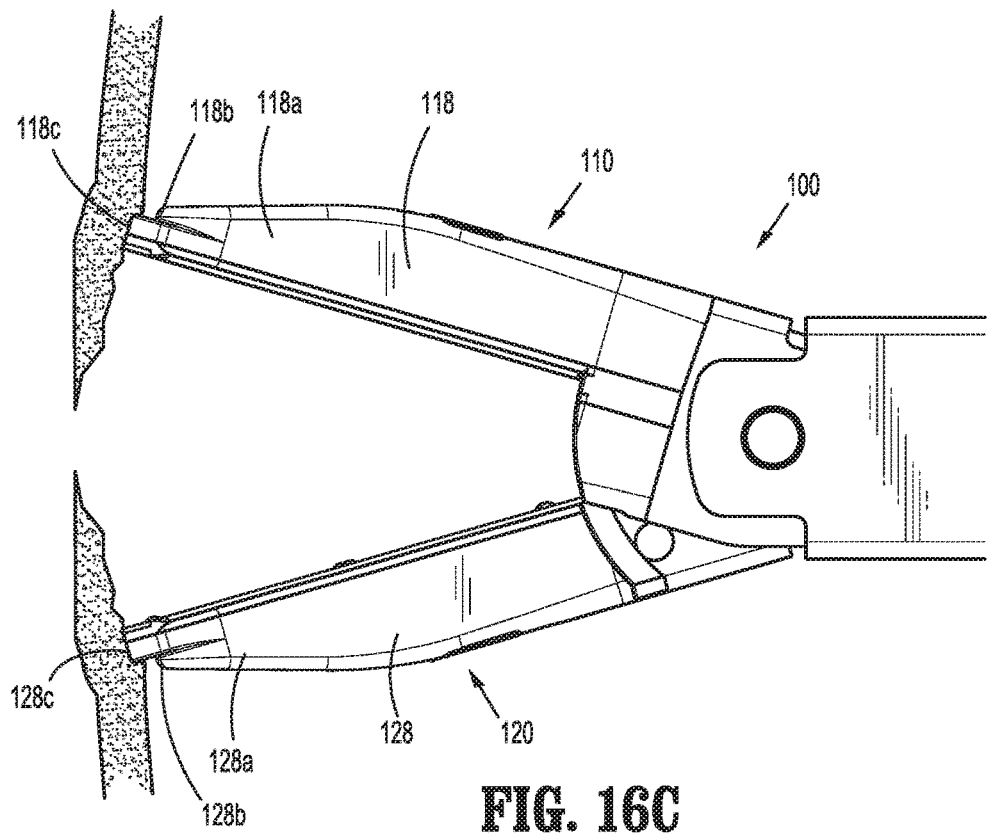
FIG. 16C is a side view of the jaw members of FIG. 15C disposed in the spaced-apart position spreading and/or dissecting tissue.
Figure 17:
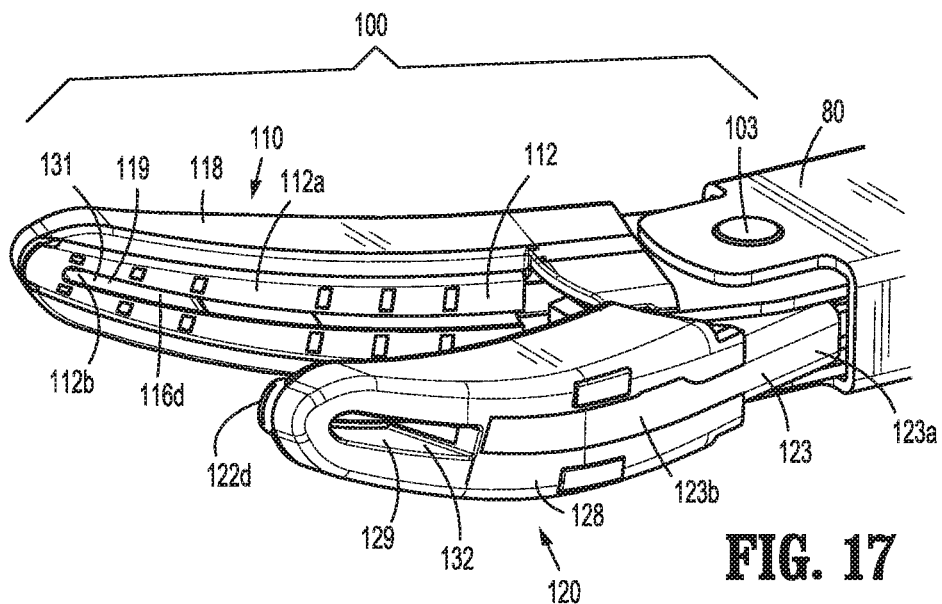
FIG. 17 is an enlarged, perspective view of the area of detail indicated as "17" in FIG. 1.
Figure 18:
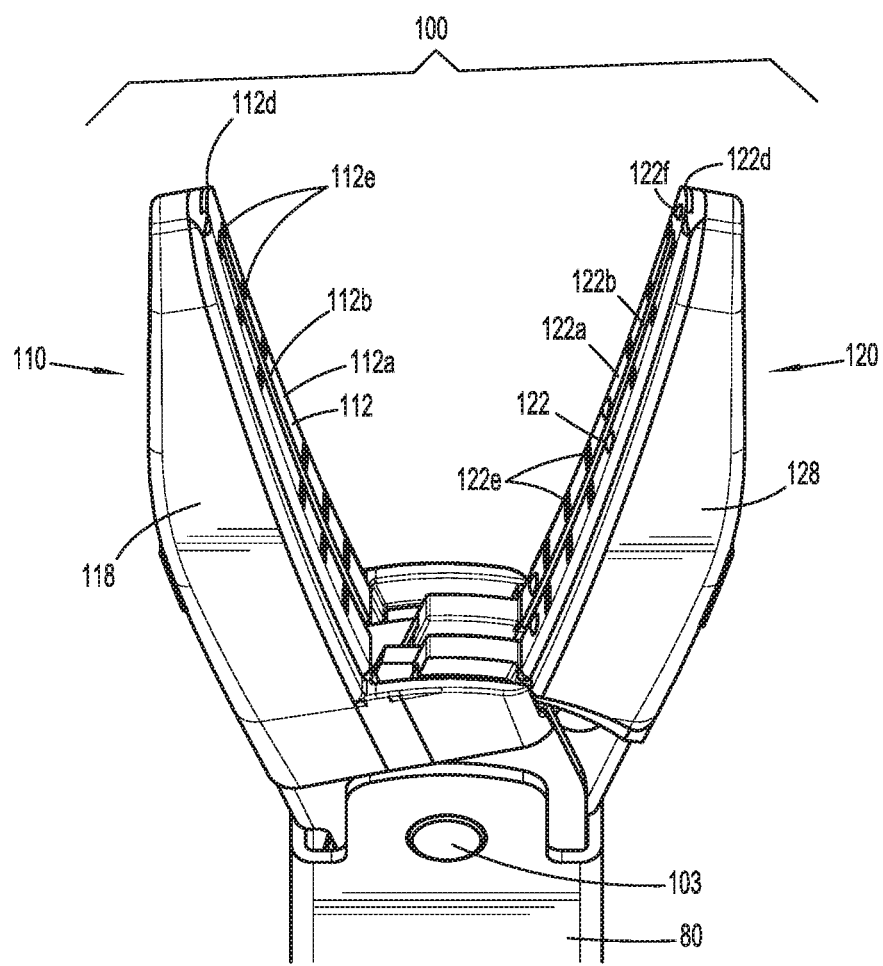
FIG. 18 is a front, perspective view of the distal end of the surgical instrument of FIG. 1 with the jaw members disposed in the spaced-apart position.

Referring to FIGS. 15C, 15C', and 16C, in some embodiments, in addition to or as an alternative to including shelves 118b, 128b, the distal ends of outer housings 118, 128 of jaw members 110,120 define extensions 118c, 128c that are relatively narrow and relatively small-radiused as compared to body portions 118a, 128a of housings 118, 128. These extensions 118c, 128c facilitate pressing the distal ends of jaw members 110, 120 further into tissue (see FIG. 15C) to ensure a relatively large contact area of tissue against shelves 118*b*, 128*b* upon moving jaw members 110, 120 to the spaced-apart position (see FIG. 16C), thus facilitating the spreading and/or dissecting of tissue.

With reference to FIGS. 15D, 15D', and 16D, in some embodiments, the distal ends of outer housings 118, 128 of jaw members 110, 120 are cut-back to define angled surfaces 118*d*, 128*d* that define an angle "ϕ" relative to the perpendicular extending from the distal ends of jaw members 110, 120 (see FIG. 16D). Angled surfaces 118*d*, 128*d*, similarly as with the previous embodiments, facilitate the pressing of the distal ends of jaw members 110, 120 further into tissue (see FIG. 15D) as well as the retention of tissue while spreading and/or dissecting tissue.

Figure 35:
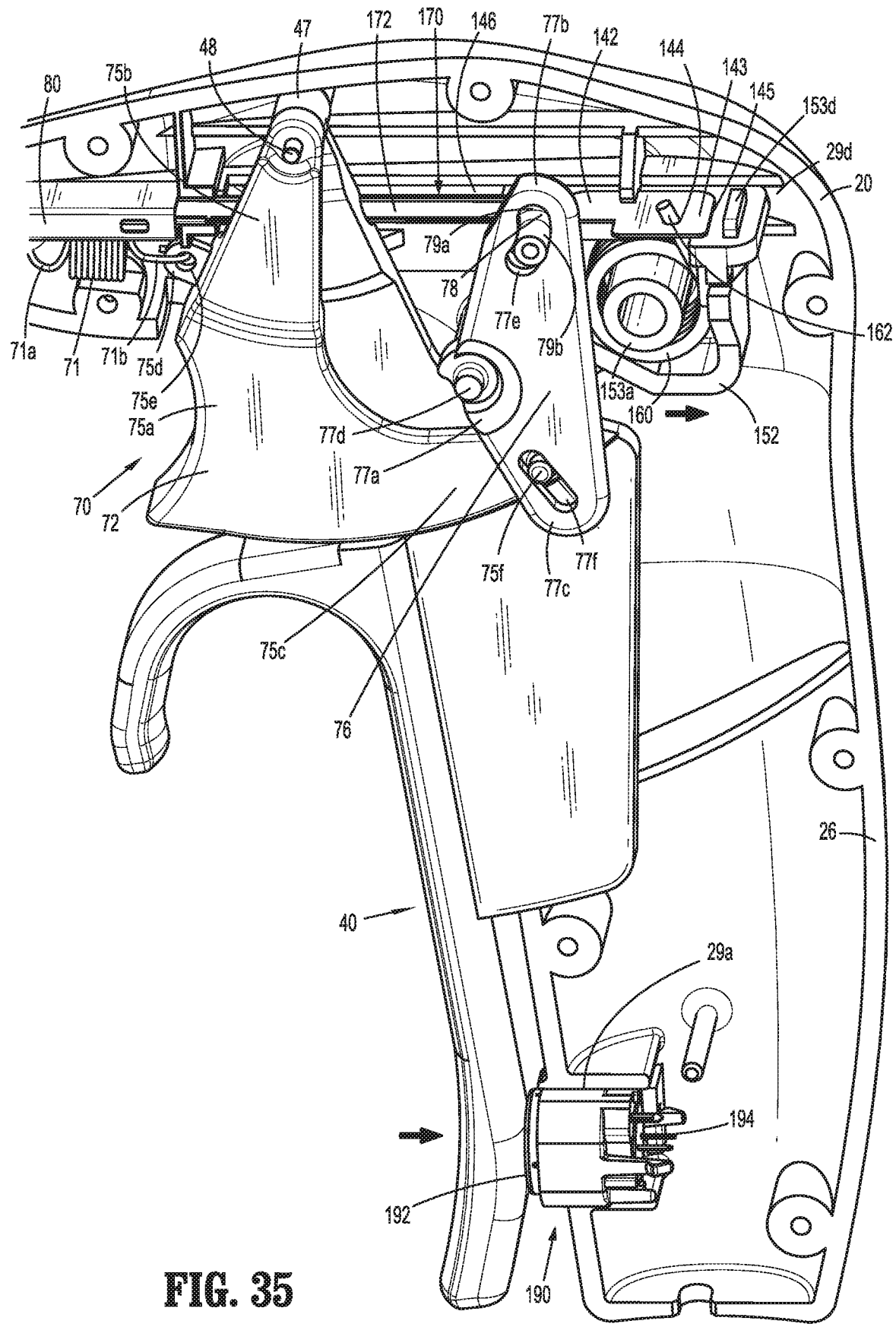
FIG. 35 is a top, perspective view of the proximal end of the surgical instrument of FIG. 1 with the movable handle disposed in an activated position and a portion of the housing removed to illustrate the internal components thereof.

Referring again to FIGS. 7-12, trigger assembly 70, as mentioned above, is operably coupled to knife assembly 170 to enable selective translation of knife blade 174 of knife assembly 170 relative to end effector assembly 100. Trigger assembly 70 includes trigger 72 and a linkage 76. Trigger 72 includes a grasping portion 75*a* which includes the concave trigger surface 73, a pivot extension 75*b* extending upwardly from grasping portion 75*a*, and a proximal extension 75*c* extending proximally from grasping portion 75*a*. Grasping portion 75*a* also includes a tab 75*d* extending distally therefrom. Tab 75*d* defines an aperture 75*e* configured to retain movable end 71*b* of biasing member 71 therein. As noted above, fixed end 71*a* of biasing member 71 is engaged via retention pin 29*f* of first housing component 22*a* of housing 20. In this manner, biasing member 71 serves to bias trigger 72 distally towards an un-actuated position (FIG. 35).

Pivot extension 75*b* of trigger 72 is pivotably coupled to housing 20 via pivot pin 48, which is engaged within and extends between pivot apertures 29*c* of first and second housing components 22*a*, 22*b* of housing 20. It is noted that pivot pin 48 is shared by both trigger 72 and movable handle 40; that is, both trigger 72 and movable handle 40 are pivotable about the same point relative to housing 20. Proximal extension 75*c* of trigger 72 includes a post 75*f* that, as detailed below, is operably engaged within cam slot 77*e* of linkage 76.

Figure 36:
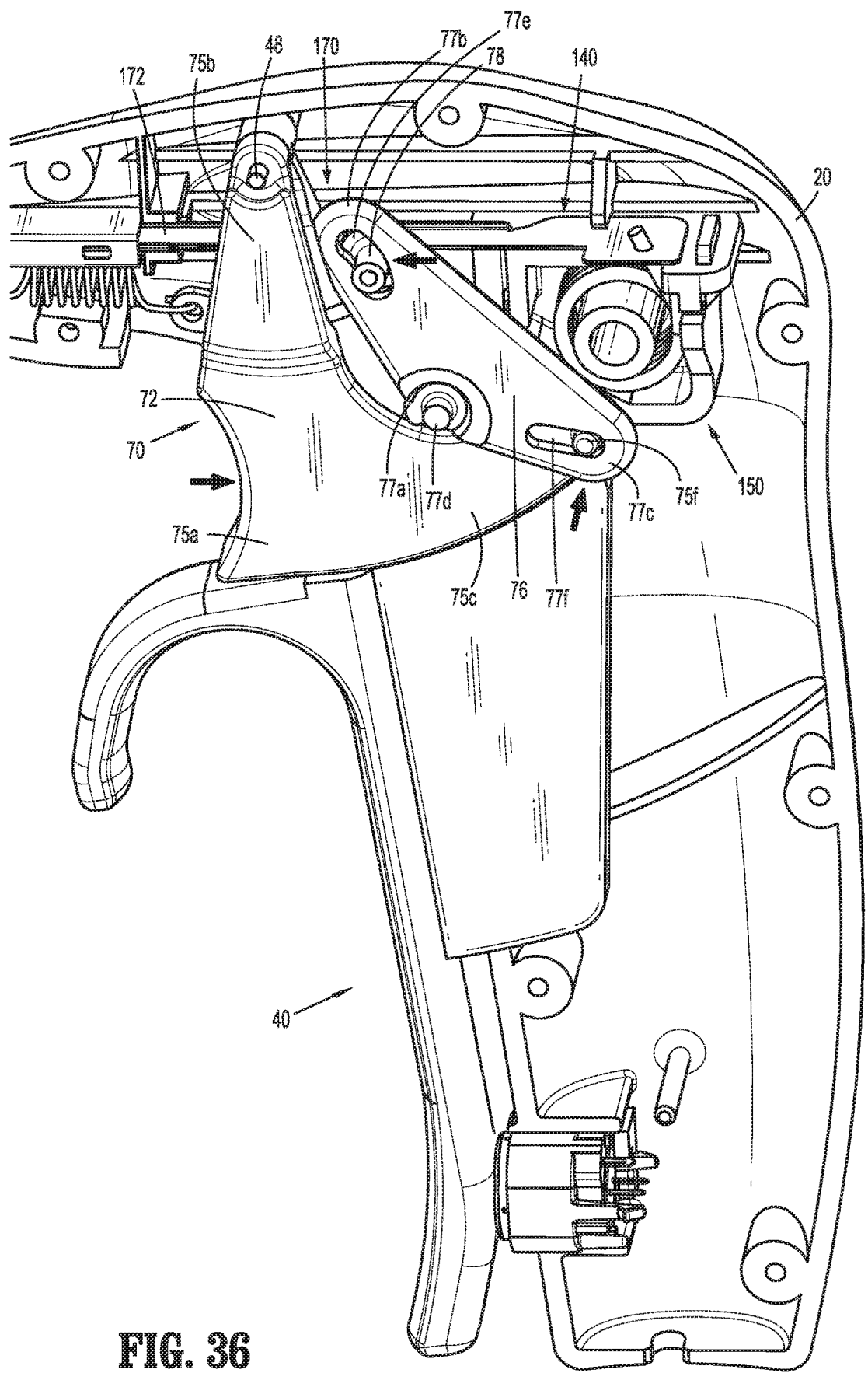
FIG. 36 is a top, perspective view of the proximal end of the surgical instrument of FIG. 1 with the trigger disposed in an actuated position and a portion of the housing removed to illustrate the internal components thereof.
Figure 37:
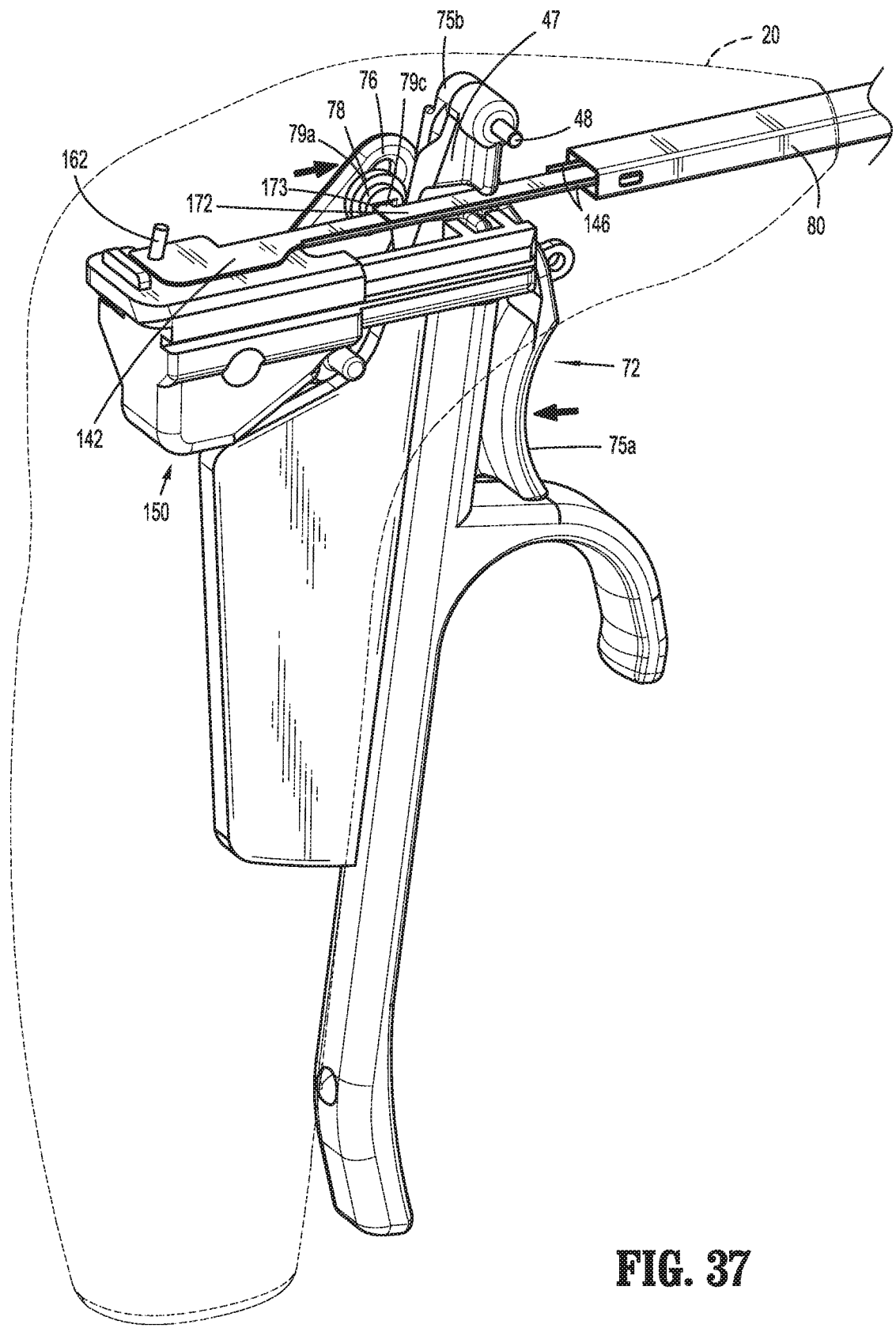
FIG. 37 is a rear, perspective view of the handle, trigger, and drive assemblies of the surgical instrument of FIG. 1 with the movable handle disposed in the activated position and the trigger disposed in the actuated position.

Linkage 76 serves to operably couple trigger 72 with knife assembly 170 such that pivoting of trigger 72 from the un-actuated position (FIG. 35) to the actuated position (FIG. 36) advances knife blade 174 relative to end effector assembly 100 to cut tissue grasped between jaw members 110, 120, as detailed below. Linkage 76 defines a generally triangular-shaped configuration including an apex 77*a* pointing in a distal direction and a base defining upper and lower corners 77*b*, 77*c*, respectively. Apex 77*a* includes a peg 77*d* that is configured for receipt within pivot boss 29*e* of first housing component 22*a* to pivotably couple linkage 76 relative to housing 20 about apex 77*a* thereof. A cam slot 77*e*, 77*f* is defined through linkage 76 adjacent upper and lower corners 77*b*, 77*c*, respectively. A coupling pin 78 operably couples cam slot 77*e* with knife plate 172 of knife assembly 170. More specifically, coupling pin 78 includes a cap 79*a* defining a slot 79*c* (FIG. 9) configured to receive finger 173 of knife plate 172 and a rod 79*b* that is operably engaged within cam slot 77*e*. As noted above, post 75*f* of proximal extension 75*c* of trigger 72 is operably engaged within cam slot 77*f*.

As a result of the above-detailed configuration of trigger assembly 70, pivoting of trigger 72 between the un-actuated and actuated positions (FIGS. 35 and 36, respectively) urges linkage 76 to pivot relative to housing 20 ultimately such that coupling pin 78 is urged to translate longitudinally within and relative to housing 20. As finger 173 of knife plate 172 is engaged with coupling pin 78, such longitudinal translation of coupling pin 78 is imparted to knife plate 172 for translating knife blade 174 between retracted and extended positions (FIGS. 29-34 and 38-40, respectively) relative to end effector assembly 100, as detailed below.

Knife assembly 170, as noted above, includes a knife plate 172 defining a finger 173 at the proximal end thereof. Knife plate 172 extends distally through housing 20 and shaft 80 atop drive plate 142 and is slidably engaged therewith via receipt of each end of knife plate 172 within track edges 146 of drive plate 142. Knife assembly 170 further includes knife blade 174 integrally formed with or otherwise engaged to knife plate 172 and extending distally therefrom. Knife blade 174 defines a width less than the combined thickness of jaw members 110, 120 at the proximal ends thereof but greater than or equal to the combined thickness of jaw members 110, 120 at the distal ends thereof. Knife blade 174 further defines an elongated opening 176 extending longitudinally therethrough. Elongated opening 176 permits knife blade 174 to be slidably disposed about pivot pin 103 and cam pin 105. More specifically, elongated opening 176 defines a first portion 177*a* having a first width configured to slidably receive pivot pin 103 and a second portion 177*b* having a second width configured to slidably receive cam pin 105 but sufficiently small to inhibit receipt of the larger-diameter pivot pin 103 therein.

As appreciated in view of the above, handle assembly 30, slider assembly 150 of drive assembly 1450, and trigger assembly 70 enable efficient assembly of instrument 10 in that these components may be operably positioned within housing 20 and relative to one another via a top-down assembly process.

Turning now to FIGS. 22-40, the use and operation of instrument 10 is described. Initially, as illustrated in FIGS. 22-24, 29, 31, and 33, movable handle 40 is disposed in the initial position and, correspondingly, jaw members 110, 120 are disposed in the spaced-apart position. More specifically, with movable handle 40 in the initial position, engagement bulge 51 is disposed in a distal-most position such that slider assembly 150 is disposed in a distal-most position. With slider assembly 150 disposed in its distal-most position, torsion spring 160 is less-tensioned and second leg 162 of torsion spring 160 retains drive plate 142 in a distal-most position. Torsion spring 160 is less-tensioned but not fully un-tensioned in the initial position of movable handle 40. This configuration maintains a pre-load on drive assembly 140 such that, as noted above, backlash due to the complete removal of tension from torsion spring 160 as jaw members 110, 120 move from the approximated position back to the spaced-apart position is eliminated. Drive plate 142 is inhibited from moving proximally relative to slider assembly 150 in this position due to the abutment of the proximal edge 145 of drive plate 142 with abutment rib 153*d* of proximal housing 152 of slider assembly 150. Further, in this distal-most position of drive plate 142, drive plate 142 maintains cam pin 105 at the distal ends of cam slots 114*b*, 124*b* and, thus, jaw members 110, 120 are maintained in the spaced-apart positon.

Figure 22:
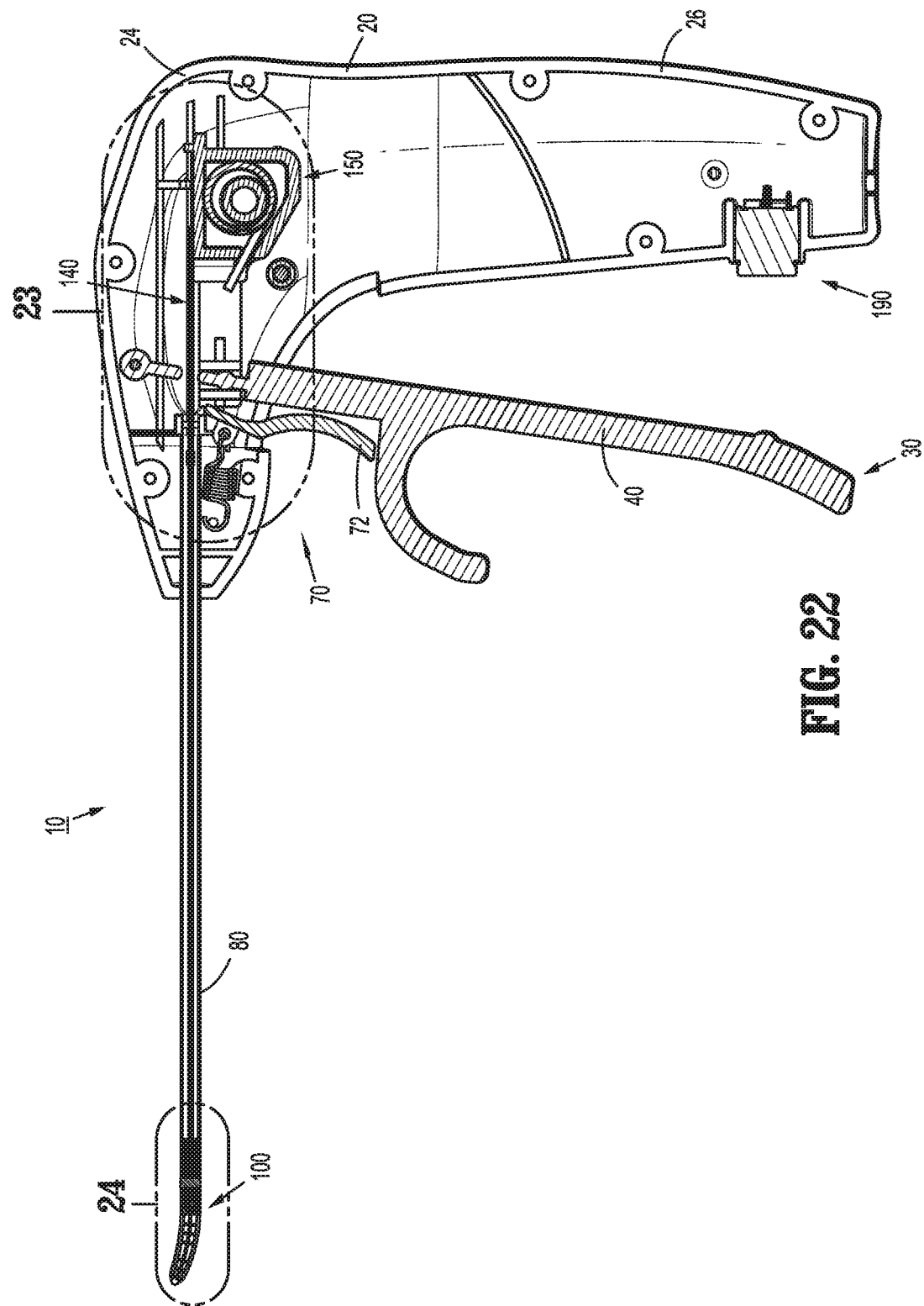
FIG. 22 is a side, cross-sectional view taken along section line "22-22" of FIG. 1.
Figure 22A:
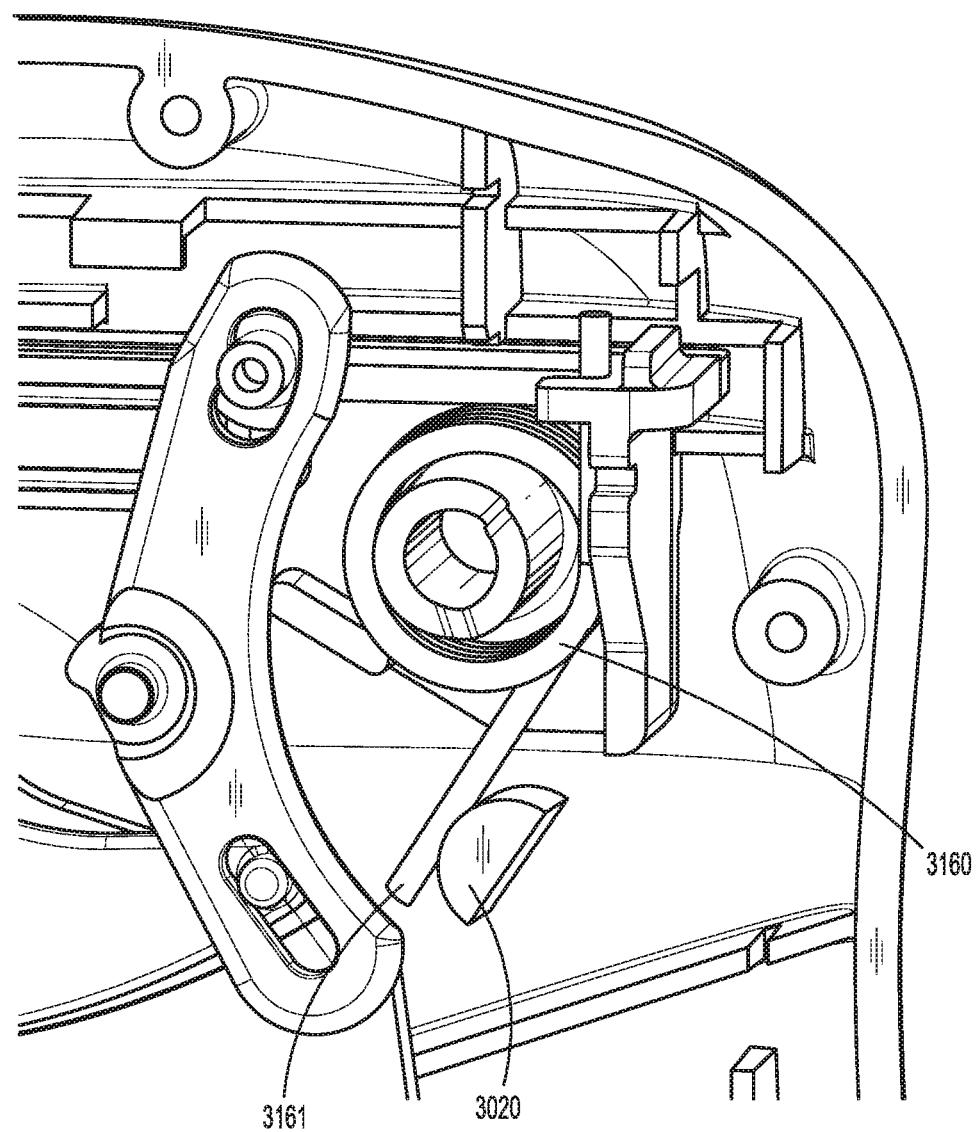
FIG. 22A is a side, cross-sectional view of the proximal end of the surgical instrument of FIG. 1 incorporating another configuration of the torsion spring provided in accordance with the present disclosure.
Figure 23:
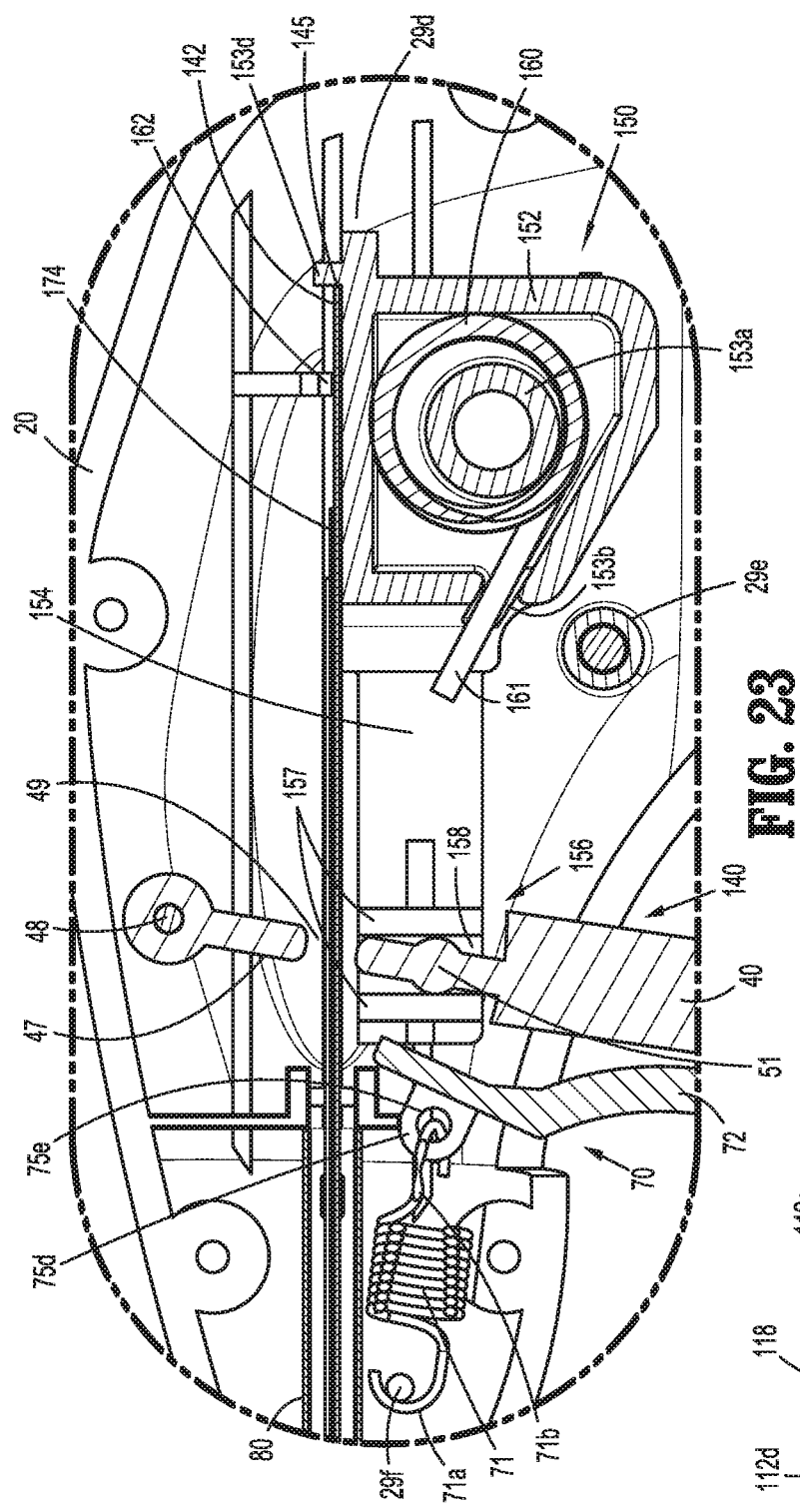
FIG. 23 is an enlarged, side, cross-sectional view of the area of detail indicated as "23" in FIG. 22.
Figure 24:
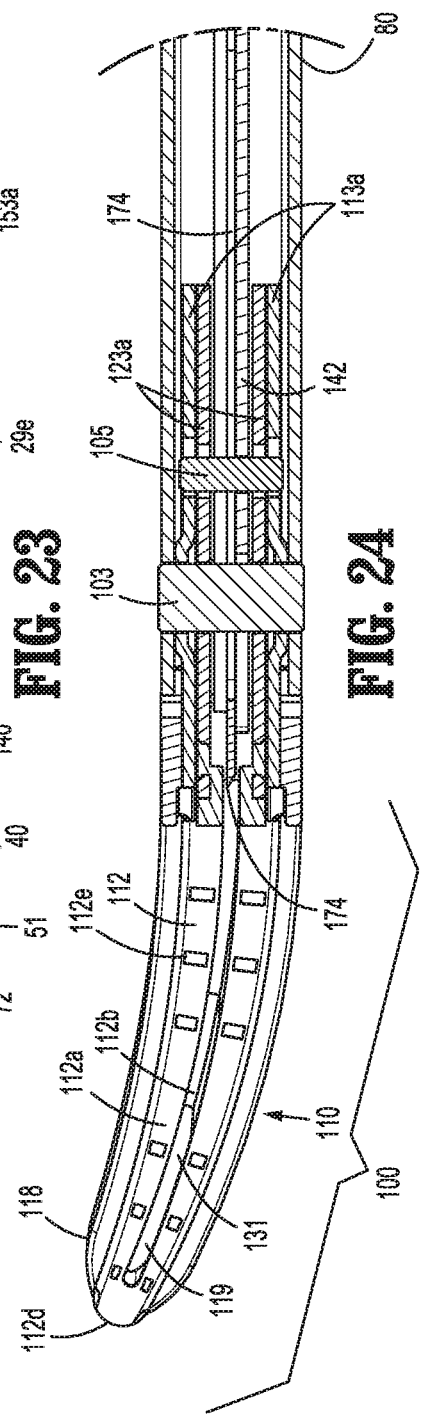
FIG. 24 is an enlarged, side, cross-sectional view of the area of detail indicated as "24" in FIG. 22.
Figure 25:
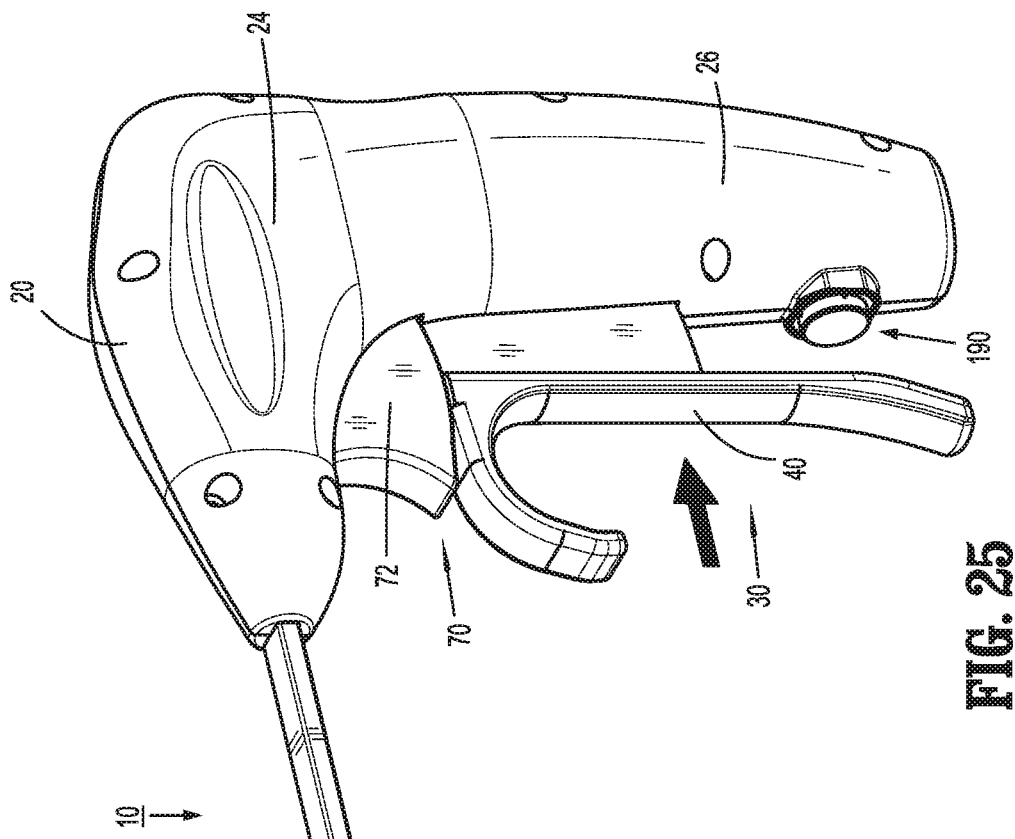
FIG. 25 is a perspective view of the surgical instrument of FIG. 1 with the movable handle disposed in a compressed position and, accordingly, the jaw members disposed in the approximated position.
Figure 26:
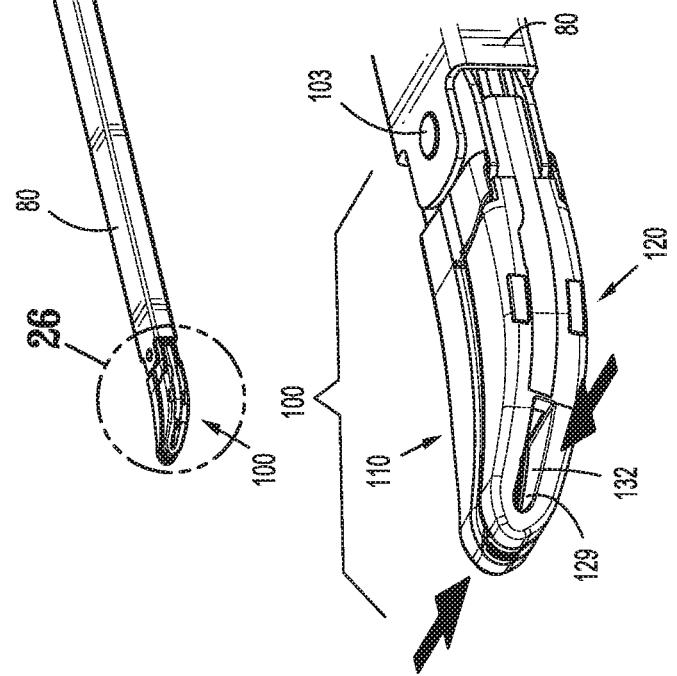
FIG. 26 is an enlarged, perspective view of the area of detail indicated as "26" in FIG. 25.

Turning for the moment to FIG. 22A, in some embodiments, rather than first leg 161 of torsion spring 160 (FIGS. 10-11) being fixed relative to proximal housing 152 of slider assembly 150, a torsion spring 3160 may be provided including a first leg 3161 that extends through a slot 3153*b* defined within proximal housing 152 and is positioned to abut a block 3020 mounted within or monolithically formed with housing 20. As a result of this configuration, torsion spring 3160 provides the additional function of biasing slider assembly 150 distally, thereby biasing jaw members 110, 120 towards the spaced-apart position (see FIG. 14). That is, upon movement of movable handle 40 to translate slider assembly 150 proximally (see FIG. 9), first leg 3161 of torsion spring 3160 is maintained in position via its abutment with block 3020, thereby further tensioning torsion spring 3160 such that, upon release of movable handle 40 (FIG. 9), torsion spring 3160 serves to bias slider assembly 150 distally, thereby biasing jaw members 110, 120 towards the spaced-apart position (see FIG. 14). Further, multiple blocks 3020 may be provided at different positions within housing 20 such that, during assembly, first leg 3161 of torsion spring 3160 may be positioned to abut a selected one of the blocks 3020 to achieve a desired biasing force.

Returning to FIGS. 22-24, 29, 31, and 33, trigger 72 is initially is disposed in the un-actuated position and, accordingly, knife blade 174 is disposed in the retracted position. More specifically, in the un-actuated position, trigger 72 is disposed in a distal-most position under the bias of biasing member 71 such that lower corner 77c of linkage 76, which is coupled to trigger 72 via engagement of post 75f within slot 77f, is disposed in a distal-most position. Since upper and lower corners 77b, 77c of linkage 76 are disposed on opposite sides of apex 77a, with lower corner 77c disposed in its distal-most position, upper corner 77b is disposed in a proximal-most position. With upper corner 77b disposed in its proximal-most position, knife plate 172 is likewise disposed in a proximal-most position due to the engagement of pin 78 within slot 77e. The proximal-most position of knife plate 172 corresponds to the retracted position of knife blade 174, wherein knife blade 174 is disposed between flanges 113a, 123a of jaw members 110, 120 but does not extend distally therefrom so as to avoid interference with tissue disposed between jaw members 110, 120. Further, in this position, pivot pin 103 is disposed at the distal end of first portion 177a of opening 176 of knife blade 174 and cam pin 105 is likewise disposed within first portion 177a of opening 176.

Figure 27:
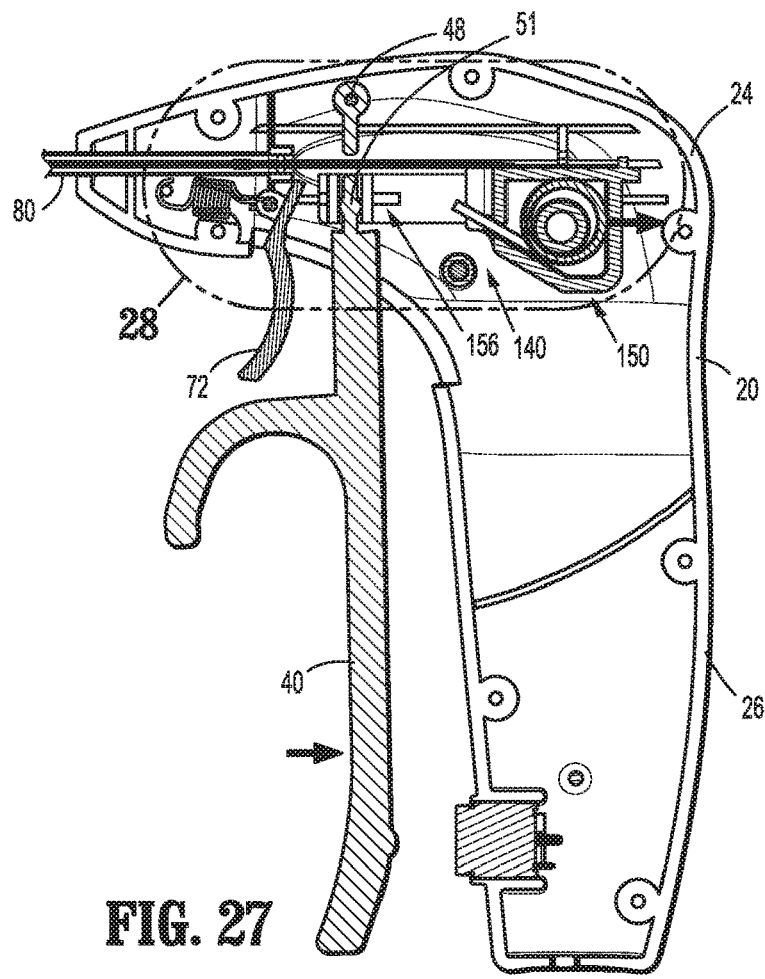
FIG. 27 is a side, cross-sectional view of the proximal end of the surgical instrument of FIG. 1.
Figure 28:
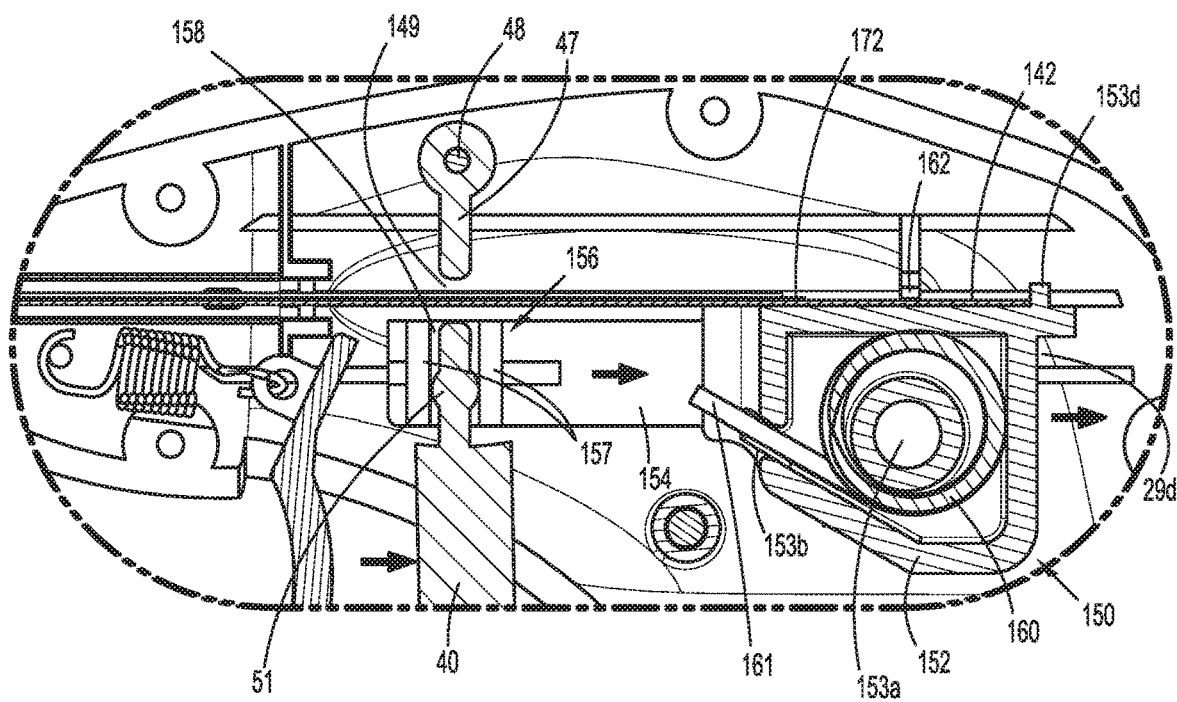
FIG. 28 is an enlarged, side, cross-sectional view of the area of detail indicated as "28" in FIG. 27.
Figure 29:
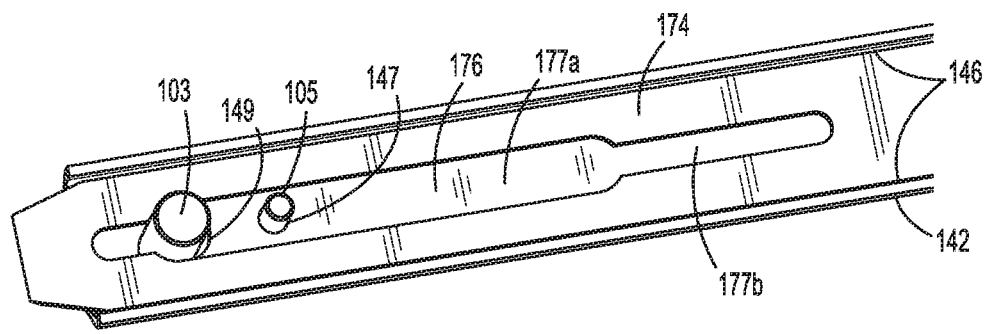
FIG. 29 is a perspective view of the distal end of the drive and knife assemblies of the surgical instrument of FIG. 1 disposed in a position corresponding to the spaced-apart position of the jaw members.
Figure 30:
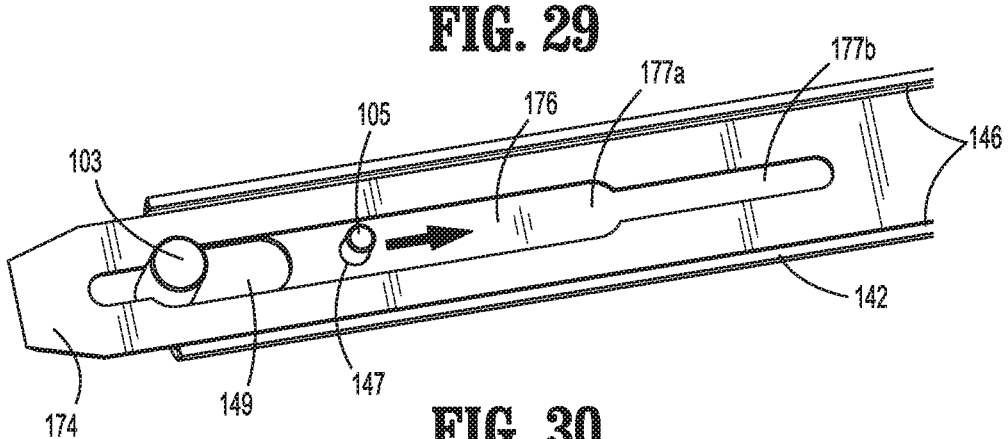
FIG. 30 is a perspective view of the distal end of the drive and knife assemblies of the surgical instrument of FIG. 1 disposed in a position corresponding to the approximated position of the jaw members.
Figure 31:
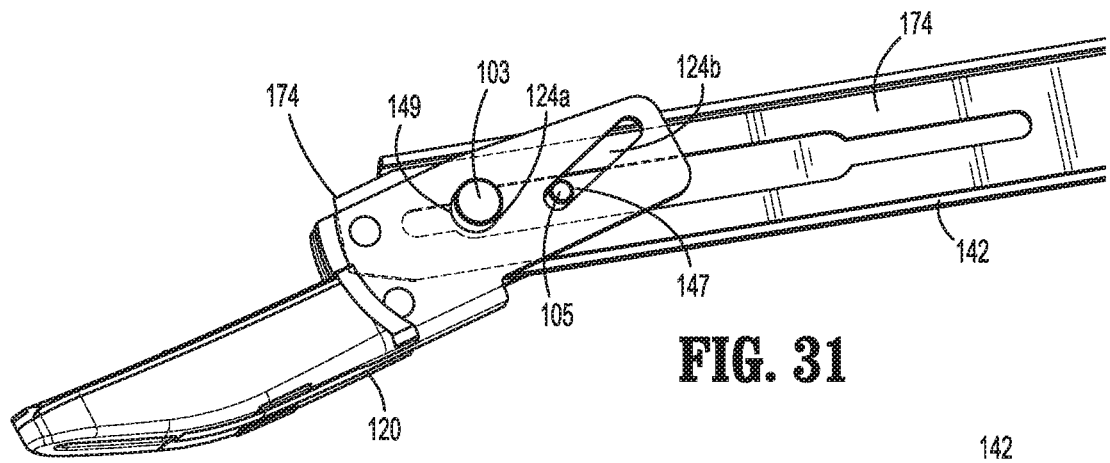
FIG. 31 is a perspective view of the distal end of the drive and knife assemblies as shown in FIG. 29 and further including one of the jaw members disposed in the spaced-apart position.
Figure 32:
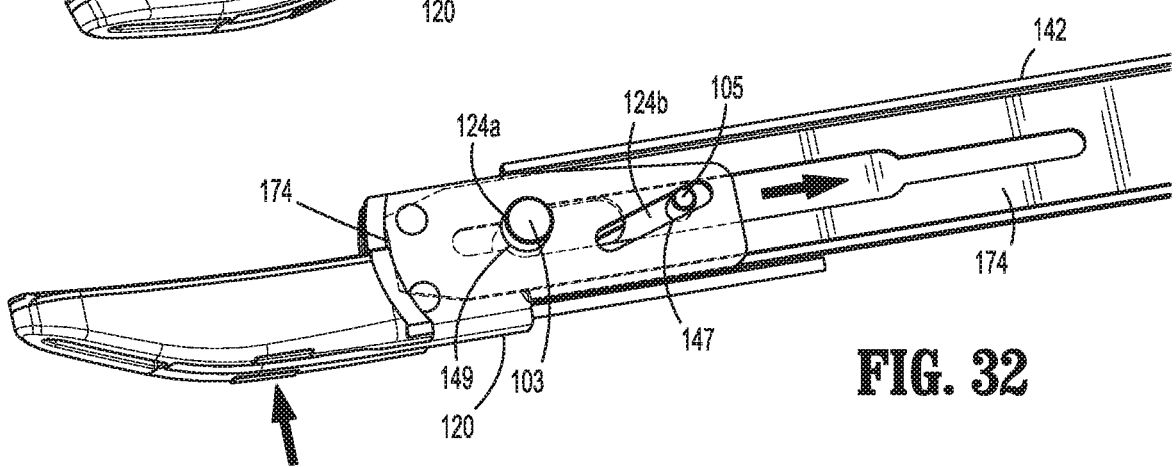
FIG. 32 is a perspective view of the distal end of the drive and knife assemblies as shown in FIG. 30 and further including one of the jaw members disposed in the approximated position.

With additional reference to FIGS. 25-28, 30, 32, and 34, in order to move jaw members 110, 120 to the approximated position to grasp tissue therebetween, movable handle 40 is pulled proximally towards fixed handle portion 26 from the initial position (FIG. 22) to the compressed position (FIG. 27). Upon such movement of movable handle 40 to the compressed position, engagement bulge 51 of movable handle 40 is moves proximally relative to housing 20, thereby urging slider assembly 150 proximally through housing 20. Torsion spring 160, in the less-tensioned state, is translated proximally together with slider assembly 150 such that second leg 162 of torsion spring 160 pulls drive plate 142 proximally in connection with the proximal translation of slider assembly 150. In other words, at this point, slider assembly 150 and drive plate 142 move in concert with one another. As drive plate 142 is pulled proximally, cam pin 105 is pulled proximally through cam slots 114b, 124b such that jaw members 110, 120 are pivoted from the spaced-apart position to the approximated position to grasp tissue therebetween.

As detailed above, movement of movable handle 40 from the initial position (FIG. 22) to the compressed position (FIG. 27) similarly translates drive plate 142 proximally, thereby moving jaw members 110, 120 to the approximated position to grasp tissue therebetween. Drive plate 142 is still inhibited from moving proximally relative to slider assembly 150 in this position due to the abutment of the proximal edge 145 of drive plate 142 with abutment rib 153d of proximal housing 152 of slider assembly 150.

At this point, with tissue grasped between jaw members 110, 120, instrument 10 may be utilized as a pliers to maneuver, manipulate, and/or reposition tissue. In particular, as noted above and illustrated in FIGS. 15 and 16, jaw members 110, 120 may be approximated adjacent a wall of tissue to pinch tissue between the distal tips of jaw members 110, 120 to enable maneuvering, manipulating, and/or repositioning thereof.

Referring to FIG. 35, in order to apply energy to tissue grasped between jaw members 110, 120 to treat tissue, movable handle 40 is compressed further towards fixed handle portion 26 to an activation position, wherein an appropriate closure force or closure force within an appropriate range, is achieved and energy activation is initiated. As movable handle 40 is moved further proximally relative to housing 20 beyond the compressed position, an appropriate closure force or closure force within an appropriate range is imparted to tissue grasped between electrically-conductive plates 112, 122 of jaw members 110, 120 regardless of the thickness or compressibility of tissue or the position of movable handle 40. This is because, upon movement of movable handle 40 from the compressed position towards the activation position, slider assembly 150 is translated proximally while drive plate 142 is maintained in position. In other words, upon movement of movable handle 40 from the compressed position to the activated position, slider assembly 150 and drive plate 142 no longer move in concert with one another. Rather, as detailed below, slider assembly 150 and drive plate 142 are decoupled to permit relative motion therebetween.

The decoupling of slider assembly 150 and drive plate 142 to permit relative motion therebetween is provided via torsion spring 160. More specifically, upon proximal movement of movable handle 40, a first force is imparted from movable handle 40, through slider assembly 150, first leg 161 of torsion spring 160, the body of torsion spring 160, and second leg 162 of torsion spring 160, to drive plate 142 to urge drive plate 142 in a proximal direction, while a second, opposite force acts on drive plate 142 and, thus, second leg 162 of torsion spring 160 in a distal direction to resist further compression of tissue between jaw members 110, 120. Once the second, opposite force exceeds the spring force of torsion spring 160, proximal movement of slider assembly 150 no longer results in proximal movement of drive plate 142 but, rather, results in further tensioning of torsion spring 160, which absorbs the force imparted thereto from movement of movable handle 40. Thus, once this point as been reached, further proximal translation of slider assembly 150 urges first end 161 of torsion spring 160 proximally, while second opposite force retains second leg 162 of torsion spring 160 in position, thereby further tensioning torsion spring 160. Since second leg 162 of torsion spring 160 is retained in position, drive plate 142 is likewise retained in position despite the proximal translation of movable handle 40 and slider assembly 150.

It is noted that, during movement of movable handle 40 from the initial position to the compressed position, as detailed above, the second, opposite force is less than the spring force of torsion spring 160 and, thus, slider assembly 150, first and second legs 161, 162 of torsion spring 160, and drive plate 142 move in conjunction with one another. Further, torsion spring 160 may be configured such that the second, opposite force exceeds the spring force of torsion spring 160 at a force corresponding to a closure pressure on tissue between 3 kg/cm$^2$ to 16 kg/cm$^2$, as it has been found that closure forces within this range facilitate sealing of tissue grasped between jaw members 110, 120. However, other forces and/or force ranges are also contemplated, e.g., for treating tissue in other manners (coagulating, cauterizing, etc.).

Continuing with reference to FIG. 35, upon achieving the activation position of movable handle 40, button activation post 196 (FIG. 7) of movable handle 40 contacts depressible button 192 sufficiently so as to depress depressible button 192 into fixed handle portion 26 to activate switch 194. Switch 194, as noted above, is disposed in electrical communication with the generator (not shown) and electrically-conductive plates 112, 122 of jaw members 110, 120, respectively, such that activation of switch 194 initiates the supply of energy to electrically-conductive plates 112, 122 to treat, e.g., coagulate, cauterize, and/or seal, tissue grasped therebetween.

Referring to FIGS. 36-40, once tissue has been treated or where it is only desired to cut tissue, knife blade 174 may be advanced between jaw members 110, 120 to cut tissue grasped therebetween. In order to advance knife blade 174 from the retracted position to the extended position, trigger 72 is pulled proximally against the bias of biasing member 71 from the un-actuated position to the actuated position. As trigger 72 is pulled proximally, post 75f is pushed proximally to urge linkage 76 to pivot counter-clockwise (from the orientation illustrated in FIG. 36) such that upper corner 77b of linkage 76 is moved distally. Distal movement of upper corner 77b urges pin 78 to translate distally due to the engagement of rod 79b of pin 78 within slot 77e of upper corner 77b of linkage 76. Distal translation of pin 78, in turn, urges knife plate 172 distally due to the engagement of finger 173 of knife plate 172 within cap 79a of pin 78.

As detailed above, movement of trigger 72 from the un-actuated position to the actuated position urges knife plate 172 distally. More specifically, knife plate 172 is urged distally such that knife blade 174 is advanced distally from the retracted position to the extended position. As knife blade 174 is advanced distally, knife blade 174 enters the knife slots of jaw members 110, 120 defined by the respective knife slots 112b, 122b of electrically-conductive plates 112, 122 and the knife slots 116c of the respective spacers 115 (only spacer 115 of jaw member 110 is illustrated). As can be appreciated, translation of knife blade 174 through the knife slots of jaw members 110, 120 to the extended position thereof divides tissue grasped between jaw members 110, 120.

Due to the fact that knife blade 174 defines a width greater than or equal to the combined thickness of jaw members 110, 120 at the distal ends thereof, as knife blade 174 is advanced distally through the knife slots, knife blade 174 may extend at least partially through windows 119, 129 and openings 131, 132 of jaw members 110, 120, depending upon the thickness of tissue grasped between jaw members 110, 120 (see FIG. 39). Further, as knife blade 174 is advanced distally, pivot pin 103 and cam pin 105 translate proximally along opening 176 eventually such that cam pin 105 extends through second portion 177b of opening 176. As pivot pin 103 is too large to extend into second portion 177b of opening 176, interference therebetween defines the distal-most extent of travel of knife blade 174. However, other components of knife assembly 170 and/or trigger assembly 70 may additionally or alternatively inhibit the extension of knife blade 174.

Upon release of trigger 72, trigger 72 and knife plate 172 are returned proximally under the bias of biasing member 71 such that knife blade 174 is returned to the retracted position. Thereafter, movable handle 40 may be returned to the initial position to release the treated and/or divided tissue.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing;

a shaft extending distally from the housing;
an end effector assembly coupled to a distal end portion of the shaft;
a drive plate slidably disposed within the shaft and operably coupled to the end effector assembly such that translation of the drive plate through the shaft and relative to the end effector assembly transitions the end effector assembly between an opened state and a closed state;
a movable handle coupled to the housing and operably coupled to the drive plate such that movement of the movable handle relative to the housing translates the drive plate through the shaft and relative to the end effector assembly;
a knife slidably disposed within the shaft and configured to translate longitudinally through the shaft and relative to the end effector assembly between a retracted position and an extended position; and
a trigger coupled to the housing and configured to pivot relative to the housing through an arc between an un-actuated position and an actuated position to move the knife between the retracted and extended positions, the trigger and the movable handle pivotably coupled to the housing about a common pivot pin.

2. The surgical instrument according to claim 1, wherein the drive plate has a pair of opposed surfaces, and the shaft has a pair of opposed long sides extending in parallel orientation relative to the pair of opposed surfaces of the drive plate.

3. The surgical instrument according to claim 2, wherein the knife has a pair of opposed surfaces extending in parallel orientation relative to the pair of opposed surfaces of the drive plate and the pair of opposed long sides of the shaft.

4. The surgical instrument according to claim 3, wherein each of the knife, the drive plate, and the pair of opposed long sides of the shaft has a planar configuration.

5. The surgical instrument according to claim 1, wherein the drive plate defines a longitudinally-extending channel in which the knife is slidably received.

6. The surgical instrument according to claim 1, further comprising a linkage operably coupling the trigger and the knife to one another.

7. The surgical instrument according to claim 6, wherein the linkage has a triangular configuration.

8. The surgical instrument according to claim 7, wherein the linkage includes an apex portion and first and second base portions, the apex portion rotatably coupled to the housing about a linkage pivot.

9. The surgical instrument according to claim 8, wherein the first base portion is disposed on a first side of the apex portion and coupled to the trigger, and the second base portion is disposed on a second side of the apex portion and coupled to the knife.

10. The surgical instrument according to claim 9, wherein, in response to movement of the trigger from the un-actuated position to the actuated position, the first base portion is configured to move proximally, the apex portion is configured to rotate about the linkage pivot, and the second base portion is configured to move distally to translate the knife longitudinally from the retracted position to the extended position.

11. The surgical instrument according to claim 1, wherein the end effector assembly includes first and second jaw members, at least one of the first or second jaw members configured to move relative to the other between a spaced-apart position and an approximated position for grasping tissue therebetween in response to movement of the movable handle relative to the housing.

12. The surgical instrument according to claim 11, wherein, in the extended position, the knife extends at least partially between the first and second jaw members to cut tissue grasped therebetween.

13. A surgical instrument, comprising:
a handle housing;
a shaft having a proximal end portion coupled to the handle housing, and a distal end portion;
an end effector assembly coupled to the distal end portion of the shaft;
a drive member having a proximal end portion received within the handle housing, and a distal end portion operably coupled to the end effector assembly such that translation of the drive member through the shaft and relative to the end effector assembly transitions the end effector assembly between an opened state and a closed state;
a movable handle coupled to the handle housing and operably coupled to the drive member such that movement of the movable handle relative to the handle housing translates the drive member through the shaft and relative to the end effector assembly;
a knife slidably disposed within the shaft and configured to translate longitudinally through the shaft and relative to the end effector assembly between a retracted position and an extended position; and
a trigger coupled to the handle housing and configured to pivot relative to the handle housing through an arc between an un-actuated position and an actuated position, wherein the trigger is operably coupled to the knife and configured to move the knife between the retracted and extended positions, the trigger and the movable handle pivotably coupled to the handle housing about a common pivot pin.

14. The surgical instrument according to claim 13, wherein the drive member has a pair of opposed surfaces, and the shaft has a pair of opposed long sides extending in parallel orientation relative to the pair of opposed surfaces of the drive member.

15. The surgical instrument according to claim 14, wherein the knife has a pair of opposed surfaces extending in parallel orientation relative to the pair of opposed surfaces of the drive member and the pair of opposed long sides of the shaft.

16. The surgical instrument according to claim 15, wherein each of the knife, the drive member, and the pair of opposed long sides of the shaft has a planar configuration.

17. The surgical instrument according to claim 13, wherein the drive member defines a longitudinally-extending channel in which the knife is slidably received.

18. The surgical instrument according to claim 13, further comprising a triangular linkage operably coupling the trigger and the knife to one another.

19. A surgical instrument, comprising:
a housing;
a shaft extending distally from the housing;
an end effector assembly coupled to a distal end portion of the shaft;
a drive plate slidably disposed within the shaft and operably coupled to the end effector assembly such that translation of the drive plate through the shaft and relative to the end effector assembly transitions the end effector assembly between an opened state and a closed state;

a movable handle coupled to the housing and operably coupled to the drive plate such that movement of the movable handle relative to the housing translates the drive plate through the shaft and relative to the end effector assembly;

a knife slidably disposed within the shaft and configured to translate longitudinally through the shaft and relative to the end effector assembly between a retracted position and an extended position;

a trigger coupled to the housing and configured to pivot relative to the housing through an arc between an un-actuated position and an actuated position to move the knife between the retracted and extended positions; and a linkage operably coupling the trigger and the knife to one another, the linkage having a triangular configuration including an apex portion and first and second base portions, the apex portion rotatably coupled to the housing about a linkage pivot, the first base portion disposed on a first side of the apex portion and coupled to the trigger, and the second base portion disposed on a second side of the apex portion and coupled to the knife.

20. The surgical instrument according to claim 19, wherein, in response to movement of the trigger from the un-actuated position to the actuated position, the first base portion is configured to move proximally, the apex portion is configured to rotate about the linkage pivot, and the second base portion is configured to move distally to translate the knife longitudinally from the retracted position to the extended position.

* * * * *